United States Patent
Zhou et al.

(10) Patent No.: US 6,387,932 B1
(45) Date of Patent: May 14, 2002

(54) SOMATOSTATIN AGONISTS

(75) Inventors: Changyou Zhou, Plainsboro; Alexander Pasternak, Princeton; Gregori Morriello, Belleville; Liangqin Guo, Edison, all of NJ (US); Yanping Pan, Gaithersburg, MD (US); Lihu Yang, Edison; Arthur Patchett, Westfield, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/595,142

(22) Filed: Jun. 16, 2000

Related U.S. Application Data

(60) Provisional application No. 60/141,096, filed on Jun. 25, 1999.

(51) Int. Cl.[7] .................... C07D 401/06; A61K 31/445
(52) U.S. Cl. ............................ 514/323; 546/201
(58) Field of Search ................... 546/201; 514/323

(56) References Cited

U.S. PATENT DOCUMENTS

| | | | |
|---|---|---|---|
| 4,225,472 A | 9/1980 | Sarantakis et al. | 260/8 |
| 4,242,347 A | 12/1980 | Huebner | 424/267 |
| 4,310,518 A | 1/1982 | Freidinger et al. | 424/177 |
| 5,360,807 A | 11/1994 | Janssens et al. | 514/318 |
| 5,710,155 A | 1/1998 | Schnorrenberg et al. | 514/255 |
| 5,767,118 A | 6/1998 | Nargund et al. | 514/226.4 |
| 5,869,489 A | 2/1999 | Shah et al. | 514/253 |
| 6,025,372 A | 2/2000 | Yang et al. | 514/316 |
| 6,057,338 A | 5/2000 | Yang et al. | 514/321 |
| 6,063,796 A | 5/2000 | Yang et al. | 514/322 |

FOREIGN PATENT DOCUMENTS

| | | |
|---|---|---|
| DE | 19636623 | 3/1998 |
| GB | 2311523 | 10/1997 |
| WO | WO 95/14666 | 6/1995 |
| WO | WO 97/43278 | 11/1997 |
| WO | WO 98/11128 | 3/1998 |
| WO | WO 98/44921 | 10/1998 |
| WO | WO 98/44922 | 10/1998 |
| WO | WO 98/45285 | 10/1998 |

OTHER PUBLICATIONS

Betoin et al., "In vitro and vivo evidence for a techykinin NK1 receptor receptor antagonist effect of vapreotide, an analgesic cyclic analog of somatostatin" CA 123:26282, 1995.
Bhattacharjee "A quantum chemical study of some model anti–inflammatory compounds" CA 117:39826, 1990.
Cavanak, T et al., Chem Abs. vol. 119, No. 23:241372d, p. 69, 1993.
Jansen et al., "Polypeptides VII Synthesis of L–and D–2, 6–diamino–4–hexnoic acid" CA 73:120889, 1970.
Hunter et al., "Identification and biosynthesis of N1, N9–bis(glutathionyl)aminopropylcadaverine in trypanosoma crizi" CA 121:296860, 1994.
Maccoss, M. et al., Chem. Abs. vol. 128:13436h, p. 386, 1998.
Patchett, A.A., et al., Proc. Natl. Acad. Sci, USA, vol. 92, pp. 7001–7005, 1995.
Rudolf, K. et al., Chemical Abstracts vol. 128:230701, 1998.
Spatola et al., "Amide bond surrogates: psudoepeptides and macrocycles" Tetrahedron, v. 44(3), pp. 821–833, 1988.

*Primary Examiner*—Bruck Kifle
(74) *Attorney, Agent, or Firm*—James L. McGinnis; David L. Rose

(57) ABSTRACT

This invention relates to non-peptide somatostatin agonist compounds which are potent with high selectivity toward the receptor subtype 2. The compounds provide an improved therapeutic index in the treatment of diabetes, cancer, acromegaly and retenosis. Many of the compounds are orally active.

12 Claims, No Drawings

SOMATOSTATIN AGONISTS

CROSS REFERENCE TO RELATED APPLICATIONS

This application claims priority from U.S. Provisional Application No. 60/141,096, filed on Jun. 25, 1999, which is incorporated by reference into this application in its entirety.

BACKGROUND OF THE INVENTION

Somatostatin (SST) is a widely distributed peptide occurring in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of somatostatin is mediated via high affinity membrane associated receptors. Five somatostatin receptors (SSTR1-5) are known (Reisine, T.; Bell, G. I. *Endocrine Reviews* 1995, 16, 427–442). All five receptors are heterogeneously distributed and pharmacologically distinct. Structure-function studies with a large number of peptidal analogs have shown that the Trp-Lys dipeptide of somatostatin is important for high-affinity binding. The availability of these receptors now makes it possible to design selectively active ligands for the sub-types to determine their physiological functions and to guide potential clinical applications. For example, studies utilizing subtype selective peptides have provided evidence that somatostatin subtype 2 receptors (SSTR2) mediates the inhibition of growth hormone release from the anterior pituitary and glucagon release from the pancreas, whereas SSTR5 selective agonists inhibit insulin release. These results imply the usefulness of SSTR2 selective analogs in the treatment of diabetes and many of the compounds of this invention have that selectivity.

In addition, the novel compounds described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis. The instant compounds inhibit cell proliferation and cause the regression of certain tumors including breast cancer and they are useful in preventing restenosis after angioplasty and to inhibit gastric motility. Their central activities include the promotion of REM sleep and an increase in cognitive function. The compounds of this invention are also remarkably reduced in size in comparison with the natural hormone and its peptide analogs such as octreotide and seglitide, which allows ease of formulation. Many of the instant compounds show activity following oral administration.

SUMMARY OF THE INVENTION

This invention relates to compounds which are agonists of somatostatin and selective toward somatostatin receptor subtype SSTR2. The compounds are not peptides. The compounds have a number of clinical uses including the treatment and prevention of diabetes, cancer, acromegaly, depression, chronic atrophic gastritis, Crohn's disease, ulcerative colitis, retinopathy, arthritis, pain both viseral and neuropathic and to prevent restenosis. Many of the compounds are orally active. Thus, it is an object of this invention to describe such compounds. It is a further object to describe the specific preferred stereoisomers of the somatostatin agonists. A still further object is to describe processes for the preparation of such compounds. Another object is to describe methods and compositions which use the compounds as the active ingredient thereof. Further objects will become apparent from reading the following description.

DETAILED DESCRIPTION OF THE INVENTION

The invention addresses a compound of structural formula I:

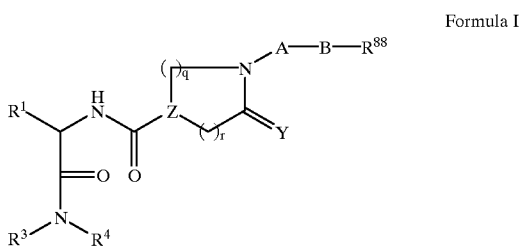

Formula I wherein:

$R^1$ is selected from the group consisting of: $C_1$–$C_6$ alkyl, aryl, aryl ($C_1$–$C_6$ alkyl), heteroaryl, heteroaryl ($C_1$–$C_6$ alkyl), ($C_3$–$C_7$ cycloalkyl)($C_1$–$C_6$ alkyl)-, ($C_1$–$C_5$ alkyl)-K—($C_1$–$C_5$ alkyl)-, aryl($C_0$–$C_5$ alkyl)-K—($C_1$–$C_5$ alkyl)-, and ($C_3$–$C_7$ cycloalkyl)($C_0$–$C_5$ alkyl)-K—($C_1$–$C_5$ alkyl)-, where K is —O—, —S(O)$_m$—, —N($R^2$)C(O)—, —C(O)N($R^2$)—, —$CR^2$=$CR^2$—, or —C≡C—, where $R^2$ and alkyl may be further substituted by 1 to 5 halogen, S(O)$_m$$R^{2a}$, 1 to 3 of OR$^{2a}$ or C(O)OR$^{2a}$, and aryl and heteroaryl are defined within, and where the aryl and heteroaryl are unsubstituted or substituted with a substituted selected from: 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), -1H-tetrazol-5-yl, —SO$_2$N(R$^2$)(R$^2$), —N(R$^2$)SO$_2$ phenyl, or —N(R$^2$)SO$_2$R$^2$;

$R^2$ & $R^5$ are selected from hydrogen, $C_1$–$C_8$ alkyl, (CH$_2$)$_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or NR$^{3a}$, where $R^{3a}$ is hydrogen, or $C_1$–$C_6$ alkyl, optionally substituted by hydroxyl; aryl is defined in the description section of the application;

$R^{2a}$ is selected from the group consisting of hydrogen and $C_1$–$C_3$ alkyl, said alkyl optionally substituted by hydroxyl;

$R^3$ is selected from the group consisting of H, $C_{1-8}$ alkyl, (CH$_2$)$_t$ aryl and (CH$_2$)$_t$ heteroaryl;

$R^4$ is CH(CO$_2$R$^2$)(CH$_2$)$_n$N(R$^2$)$_2$, CH(R$^2$)—(CH$_2$)$_n$ N(R$^2$)$_2$, CH(CO$_2$R$^2$), CHCON(R$^2$)$_2$, CH(CO$_2$R$^2$) CH$_2$W(CH$_2$)$_n$N(R$^2$)$_2$, CHR$^2$(CH$_2$)$_n$W(CH$_2$)$_n$N(R$^2$)$_2$, or is selected from R$^6$;

$R^6$ is:

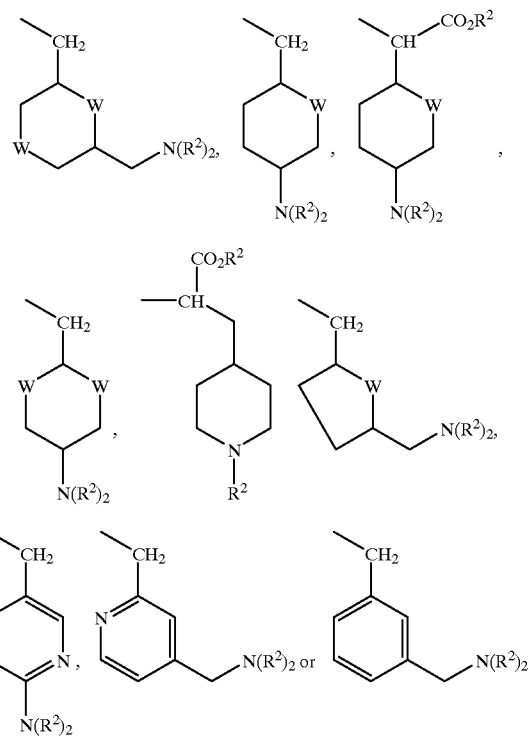

wherein $R^6$ is optionally substituted with 1 to 3 groups of $R^2$, 1 to 3 of halogen, 1 to 2 of —$OR^2$, methylenedioxy, —$S(O)_m R^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)SO_2R^2$;

alternatively,

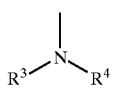

can be

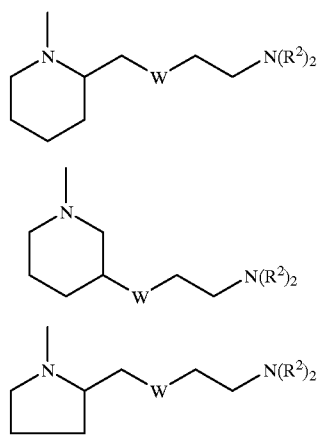

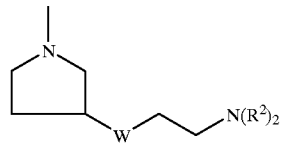

where W is selected from the group consisting of O, S, $CH_2$, $N(R^2)C(O)$ and $C(O)N(R^2)$;

Y is (H,H) or O;

Z is CH or N;

A is CO, $SO_2$,

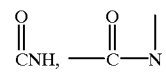

(alkyl having 1–6 carbons), $(CH_2)_x C_{3-8}$ cycloalkyl, $C_{3-8}$ cycloalkyl, aryl, heteroaryl, $(CH_2)_x$aryl, $(CH_2)_x$ heteroaryl, heterocyclyl, $C_1$–$C_6$ alkyl, wherein x is 1–6, wherein each aryl, heteroaryl, heterocyclyl, and cycloalkyl is optionally substituted with 1–6 substituents independently selected from halogen, methylenedioxy, alkyl having 1–6 carbon atoms, O-alkyl having from 1–6 carbon atoms, OH, CN,

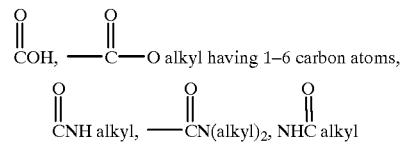

having 1–6 carbon atoms, wherein each alkyl that is either A or is a substituent on A is optionally substituted with 1–6 halogen atoms and optionally 1–3 substituents selected from aryl, OH, $NH_2$, cycloalkyl optionally having 1–4 $C_1$–$C_3$ alkyl groups,

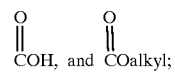

B is $C_1$–$C_6$ alkyl, cycloalkyl, NH, N(alkyl having 1–6 carbon atoms), O, or a single bond, where alkyl and cycloalkyl are as described under A and optionally substituted as under A; and $R^{88}$ is H, aryl, $(CH_2)_x$ aryl, heteroaryl, $(CH_2)_x$ heteroaryl, $C_3$–$C_8$ cycloalkyl, $(CH_2)_x$ cycloalkyl having 3–8 carbons, $C_1$–$C_6$ alkyl, NH alkyl having 1–6 carbon atoms, $N(alkyl)_2$, where each alkyl is independently a $C_1$–$C_6$ alkyl,

alkyl having 1–6 carbons, where x and each aryl, heteroaryl, cycloalkyl, and alkyl are as described under A and optionally substituted as described under A;

m is an integer from 0 to 2;

n is an integer from 0–5;

q is an integer from 0–6;

r is an integer from 0–6; and t is an integer from 0 to 3.

In preferred compounds, Formula I has the stereochemistry shown in Formula Ia:

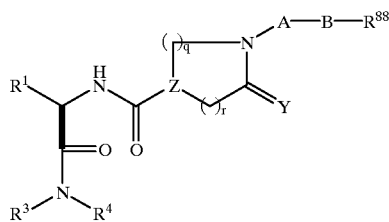

Formula Ia

Preferred compounds of the instant invention include those of Formula I and Ia in which:

$R^1$ is selected from the group consisting of: aryl ($C_1$–$C_6$ alkyl), heteroaryl($C_1$–$C_6$ alkyl), where aryl and heteroaryl is selected from: phenyl, indanyl, benzyloxy, benzothiazolyl, biphenyl, aza-indolyl, benzyl(with 1,4-butane diamine) naphthyl, quinolinyl, indolyl, pyridyl, benzothienyl, benzofuranyl, thiazolyl, and benzimidazolyl, and where the aryl and heteroaryl are unsubstituted or substituted with a substitutent selected from: 1 to 3 of $C_1$–$C_6$ alkyl, 1 to 3 of halogen, 1 to 2 of —$OR^2$, 1 to 2 of —$CF_3$, —$OCF_3$, nitro, $C(O)OR^2$, or $C(O)N(R^2)(R^2)$;

$R^2$ is selected from: hydrogen, $C_1$–$C_8$ alkyl, and $(CH_2)_t$ aryl, where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^3$ is selected from the group consisting of hydrogen, $C_1$–$C_8$ alkyl and $(CH_2)_t$ aryl;

$R^4$ is $CH(CO_2R^2)(CH_2)_nN(R^2)_2$, $CH(R^2)$—$(CH_2)_n$ $N(R^2)_2$, $CH(CO_2R^2)CH_2WCH_2CH_2N(R^2)_2$, or is selected from $R^6$;

$R^6$ is

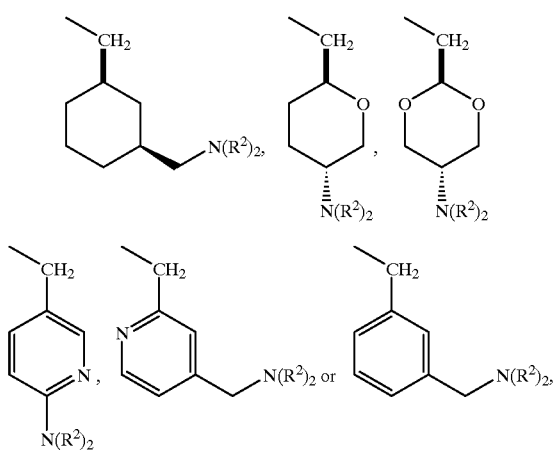

wherein $R^6$ is optionally substituted with 1 to 3 groups of $R^2$, 1 to 3 of halogen, 1 to 2 of —$OR^2$, 1 to 2 of —$CF_3$, —$OCF_3$, nitro, —$C(O)OR^2$, or —$C(O)N(R^2)(R^2)$;

optionally,

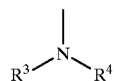

can be

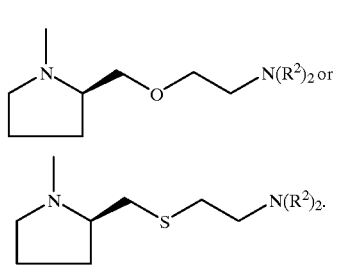

All other variables are described above.

More preferred compounds of Formula I and Formula Ia are realized when:

$R^1$ is

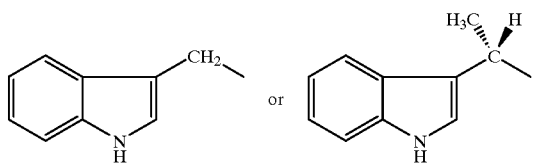

which may be substituted by 1 to 3 of $R^2$, 1 to 3 of halogen, 1 to 2 of —$OR^2$, 1 to 2 of —$CF_3$, —$OCF_3$, nitro, —$C(O)OR^2$, —$C(O)N(R^2)(R^2)$;

$R^3$ is selected from hydrogen or methyl;

$R^4$ is $CH(CO_2But)(CH_2)_4NH_2$, $CH(R^2)$—$(CH_2)_4NH_2$, $CH(CO_2But)CH_2WCH_2CH_2NH_2$, or $R^6$ wherein $R^6$ is

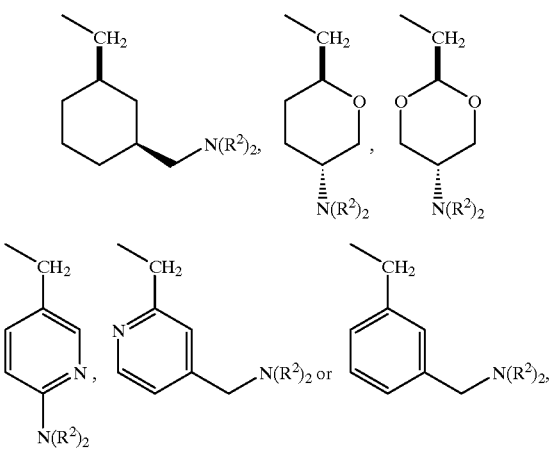

which is optionally substituted with 1 to 3 groups of $R^2$, 1 to 3 of halogen, 1 to 2 of —$OR^2$, 1 to 2 of —$CF_3$;

and all other variables are described above.

Particularly preferred embodiments of compounds of Formula Ia as described above include compounds in which:

(1) Z is CH,
  r is 1,
  q is 1, and
  Y is O; or
(2) Z is CH,
  Y is (H,H)
  r is 0 or 1, and
  q is 2 or 3; or
(3) Z is N,
  Y is (H, H)
  r is 1, and
  q is2.
In particularly preferred embodiments, "heteroaryl" in the A—B—R$^{88}$ portion of Compound I refers to benzimidazole, benzofuran, thiophene, pyridine, or indole.
Specific compounds of this invention are provided in Examples 1–23.
Particularly preferred compounds are illustrated below:
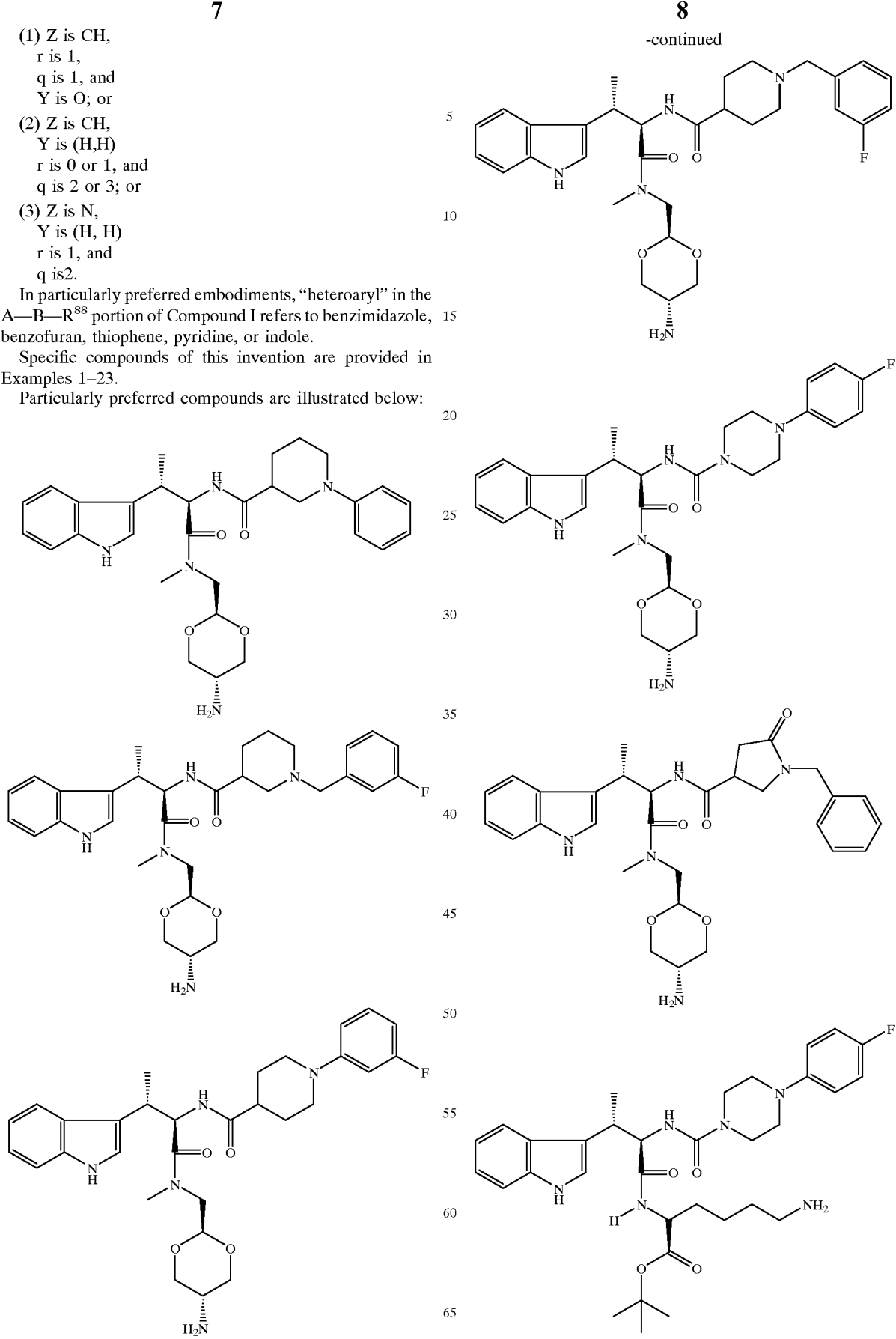

-continued

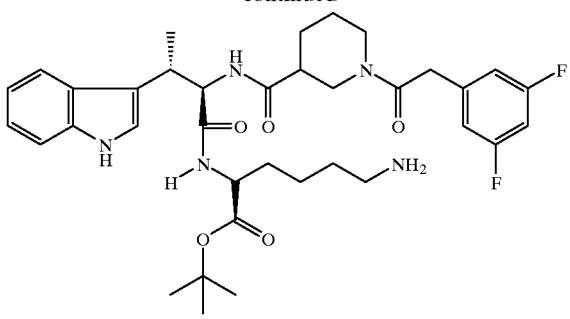

Also included in the invention is a pharmaceutical composition which is comprised of a compound of formula I in combination with a pharmaceutically acceptable carrier.

The invention also includes a method of treating diabetes, cancer, acromegaly chronic atrophic gastritis, Crohn's disease, ulcerative colitis, retinopathy, arthritis, viseral and neuropathic pain and to prevent restenosis, which comprises administering to a person or animal a compound of formula I in an amount which is effective for treating said disease or condition.

The invention is described herein in detail using the terms defined below unless otherwise specified.

The term "alkyl" refers to a monovalent alkane (hydrocarbon) derived radical containing from 1 to 15 carbon atoms unless otherwise defined and if two carbon atoms or more they may include a double or a triple bond. It may be straight, branched or cyclic. Preferred straight or branched alkyl groups include methyl, ethyl, propyl, isopropyl, butyl and t-butyl. Preferred cycloalkyl groups include cyclopentyl and cyclohexyl. The term "cycloalkyl" is also used herein to describe cyclic alkyls containing 3–8 carbon atoms in the ring.

Alkyl also includes a straight or branched alkyl group which contains or is interrupted by a cycloalkylene portion. Examples include the following:

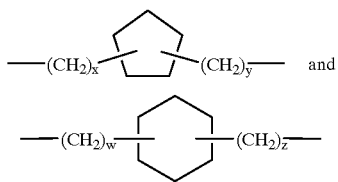

wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

Aryl refers to aromatic rings e.g., phenyl, substituted phenyl and like groups as well as rings which are fused, e.g., naphthyl, indaryl, biphenyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with from 1 to 3 groups of $C_1$–$C_{15}$ alkyl, halogen, —$OR^2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, 1H-tetrazol-5-yl, —$SO_2N(R^2)_2$—$N(R^2)SO_2$ phenyl or —$N(R^2)SO_2R^2$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups selected from 1 to 3 of $C_1$–$C_8$ alkyl, halogen, —$OR^2$, methylenedioxy, —$S(O)_mR^2$, —$CF_3$, —$OCF_3$, $N(R^2)_2$, nitro, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl or —$N(R^2)SO_2R^2$.

Heteroaryl thus includes aromatic and partially aromatic groups which contain one or more heteroatoms. Examples of this type are thiophene, oxadiazole, imidazopyridine, pyridine, oxazole, thiazole, pyrazole, tetrazole, imidazole, pyrimidine, pyrazine, benzothienyl, benzofuranyl, indolyl, azaindole, benzimidazolyl, quinolinyl, isoquinolinyl and triazine.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms. If the heterocycle contains nitrogen, then the nitrogen may be substituted with an alkyl group. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like.

Certain of the above defined terms may occur more than once in the same formula and upon such occurrence each term shall be defined independently of the other, unless it is explicitly stated that the defined terms are the same in any particular formula.

Salts encompassed within the term "pharmaceutically acceptable salts" refer to non-toxic salts of the compounds of this invention which are generally prepared by reacting the free base with a suitable organic or inorganic acid. Representative salts and esters include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom to which RI is attached, it has been found that compounds are more active as somatostatin agonists and, therefore preferred, having the stereochemistry of Formula Ia. The stereochemical representation places $R^1$ and the N-substituent in the plane of the structure with the C=O group above. This configuration corresponds to that present in a D-amino acid. In most cases, this is also designated an R-configuration, although this will vary according to the value of $R^1$ used in making R- or S-stereochemical assignments. In addition, configurations of some of the most preferred compounds of this invention are indicated. Stereochemical centers at other positions in the molecular will result in diastereomers. These diastereomers can be synthesized independently and separated by chromatography if desired. Their absolute stereochemistry may be determined by the x-ray crystallography of crystalline products or crystalline intermediates which are derivatized, if necessary, with a reagent containing an asymmetric center of known absolute configuration.

The term "pharmacologically effective amount" shall mean that amount of a drug or pharmaceutical agent that will elicit the biological or medical response of a tissue, system, animal or human that is being sought by a researcher or clinician.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of the present invention to act as somatostatin agonists makes them useful as pharmacologic agents for mammals, especially for humans, for the treatment and prevention of disorders wherein somatostatin itself or the hormones it regulates may be involved.

Examples of such disorders have been noted earlier and include diabetes, acromegalym neuropathic pain, restenosis, retinopathy, depression, arthritis and cancer. The instant compounds can also be used in combination with other therapeutic agents which are useful in treating these conditions. For example, for diabetes treatment these agents include metformin or other biguanides, acarbose, sulfonylureas, thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I-glp-I and available satiety-promoting agents such as dexfenfluramine.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |
| KBMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

The instant compounds can be effective to inhibit the secretion of various hormones and trophic factors in mammals. They may be used to suppress certain endocrine secretions, such as GH, insulin, glucagon and prolactin, in the treatment of disorders such as acromegaly; endocrine tumors such as carcinoids, vipomas, insulinomas and glucagonomas; or diabetes and diabetes-related pathologies, including retinopathy, neuropathy and nephropathy. The compounds may also be used to suppress exocrine secretions in the pancreas, stomach and intestines, for treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the instant compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty. Somastostatin in the brain inhibits the neuronal release of substance P(NK-1) and NK-1 antagonists have been shown to have a marked use as an antidepressant agent. Accordingly, the instant compounds are also useful in treating depression.

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis and oesophagal varices, the compounds of the invention can provide cytoprotection.

The preparation of compounds of Formula I of the present invention may be carried out in sequential or convergent synthetic routes. The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMF or mixtures thereof, followed by addition of the second amine and a base such as NMM, TEA or DIEA. The uses of protective groups for amines and carboxylic acids to facilitate the desired reaction and minimize undesired reactions are well documented. Conditions required to remove protecting groups which may be present can be found in Greene, T, and Wuts, P. G. M., *Protective Groups in Organic Synthesis*, John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula Ia or Ib are, in many cases, commercially available, where the protecting group ($P^1$) is, for example, methyl, allyl or benzyl groups. Other protected amino acid can be prepared by literature methods (Williams, R. M. *Synthesis of Optically Active α-Amino Acids*, Pergamon Press: Oxford, 1989).

Preparative Schemes

The compounds of the present invention can be prepared readily according to the following Schemes or modifications thereof using readily available starting materials, reagents and conventional synthesis procedures. Purification procedures include crystallization, normal phase and reverse phase chromatography. In these reactions, it is also possible to make use of variants which are readily apparent to those of ordinary skill in this art, but are not mentioned herein in great detail. The definitions for $R^1$, $R^2$, $R^{2a}$, $R^3$, $R^4$, $R^5$, Y, Z, W, etc., are described above unless otherwise stated. The symbol —Q—NH$_2$ in Schemes 1–6 is equivalent to -$R^4$ as previously defined, where R4 is not part of a heterocyclic ring (i.e. it is alicyclic). The symbols n and m in Schemes 1–6 are equivalent to q and r elsewhere in this application. $R^2$ in Schemes 1–6 is $R^3$ in the remainder of the application. Schemes 1–6 are descriptive of synthetic routes for making a preferred stereoisomer, but can be readily used for the other stereoisomer as well.

Intermediate 1 can be synthesized as described in Scheme 1. The amide formation between the monoprotected diamine 1a and the protected amino acid 1b, was conveniently carried out under usual amide formation reactions using EDC or equivalents such as PyBOP, PyBrOP without or with DIEA. Selective removal of the P3 protecting group can be achieved by either acidic cleavage with TFA/DCM, MeSO$_3$H/MeOH or 4N HCl/Dioxane when $P^3$ is BOC, or basic cleavage with 25% piperidine when $P^3$ is FMOC. Intermediate 1 can be used as a common intermediate for the synthesis of somatostatin agonists with variation of the rest of the molecule of Formula 2 and 5 as shown in Scheme 1.

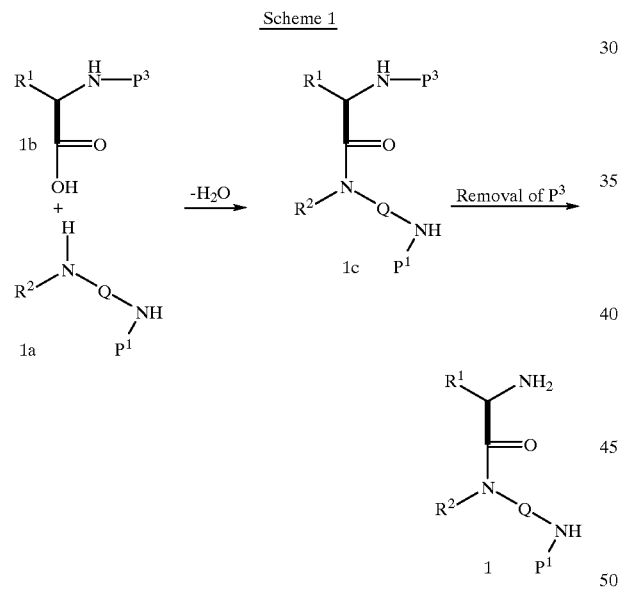

Scheme 1

The preparation of acid intermediates of formular 2 can be achieved as shown in Scheme 3. Starting from commercially available 2a (Z=CH) such as ethyl nipecotate or isonipecotate, the intermediatec 2c (Z=CH) can be obtained by N-alkylation, N-acylation and N-sulfonylation of 2a with alkyl halides, acyl chloride and sulfonyl chloride in the presence of base, or N-arylation by Buchwald Reaction. The resulting 2c is then subjected to saponification (Methyl and Ethyl esters) or acidic hydrolysis (tert-butyl esters) to afford 2 suitable for further coupling. Several esters 2c are commerically available, therefore, they are directly saponified to give the acids 2. Most of N-monosubstituted piperizanes or other cyclic diamines 5a are commercially available. 5a can also be easily made by N-substitution of N-Boc/Cbz-piperizanes 2a (Z=N) and TFA cleavage (Boc) or hydrogenolysis of 2c (Z=N).

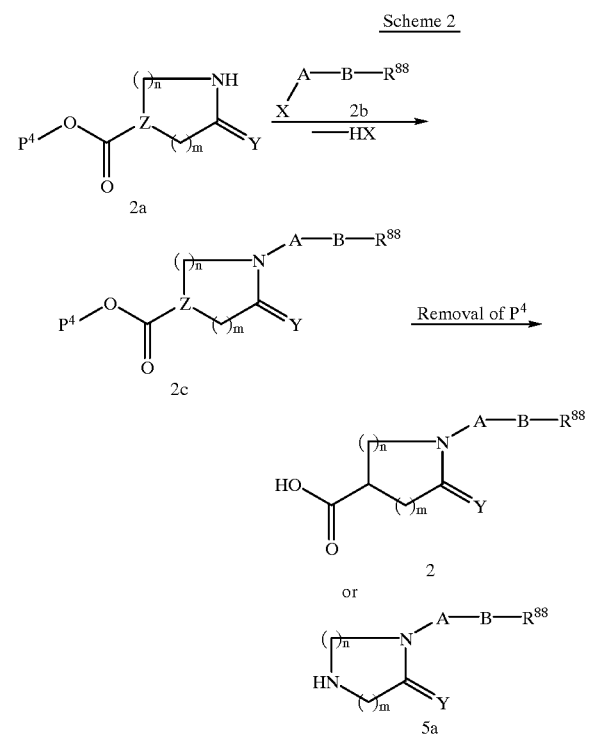

Scheme 2

Intermediates 3 are prepared as shown in Scheme 4. The normal coupling of the intermediates 1 and the protected amino acids 3a are carried out both in solution and on solid phase using the standard amide bond formation reagents. $P^2$ is removed by acidic conditions (BOC, in solution chemistry) or by piperidine/DMF (FMOC, on solid phase).

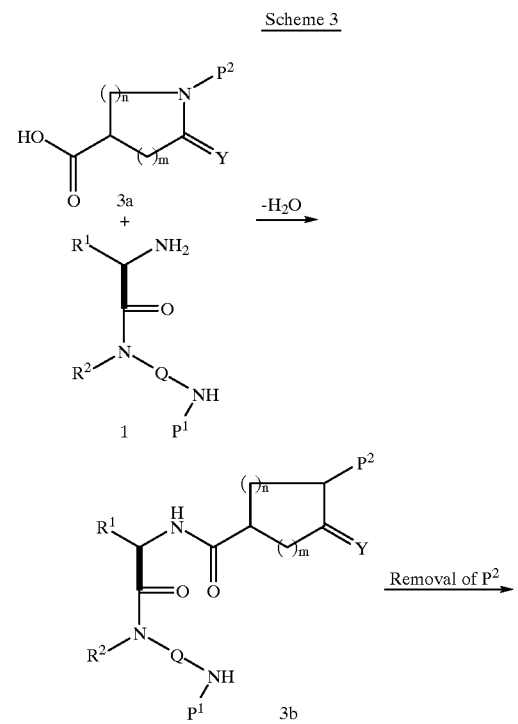

Scheme 3

-continued

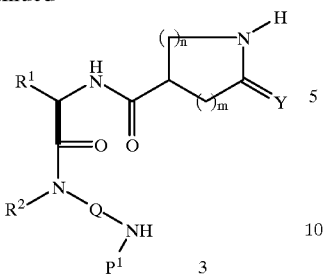

Intermediates of Formula 2 can be coupled to intermediates of formula 1 to afford compounds of Formula 4a under standard peptide coupling reaction conditions. Further deprotection of $P^1$ gave the final products as HCl or acetic acid salts suitable for various bioassays.

Scheme 4

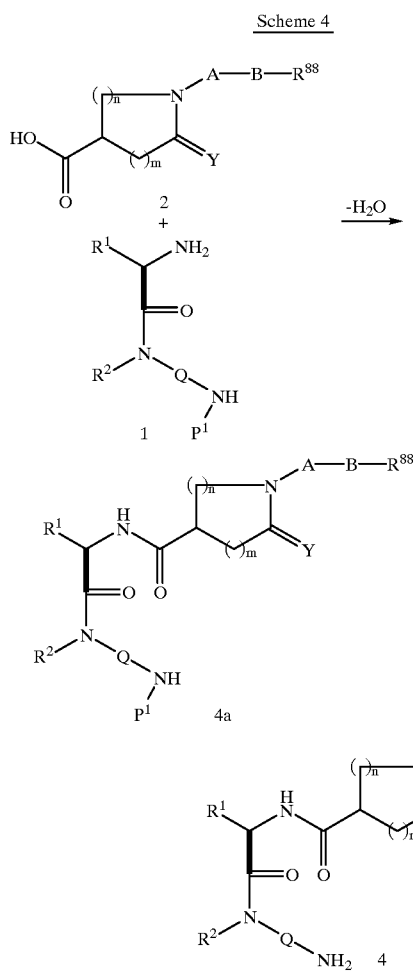

Another approach to make the final products 4 is based on derivatizing intermediates 3 with compounds 2b. Four types of reactions can be used to prepare intermediate 4a: a) alkylation with alkyl halides in the presence of a non-nucleophilic base such as DIEA; b) reductive alkylation with aldehydes and reducing agents such as NaCNBH3; c) acylation with free acids with coupling agents such as PyBOP, EDC, etc.; d) urea formation with isocyanates or active chlorocarbamides; f) sulfonamide formation with sulfonyl chlorides in the presence of DIEA. Removal of the proctecting group $P^1$ in 4a by hydrogenolysis ($P^1$=Cbz) or cleavage with acetic acid ($P^1$=2-chlorotrityl resin) afforded final prodcuts as HCl or acetic acid salts.

Scheme 5

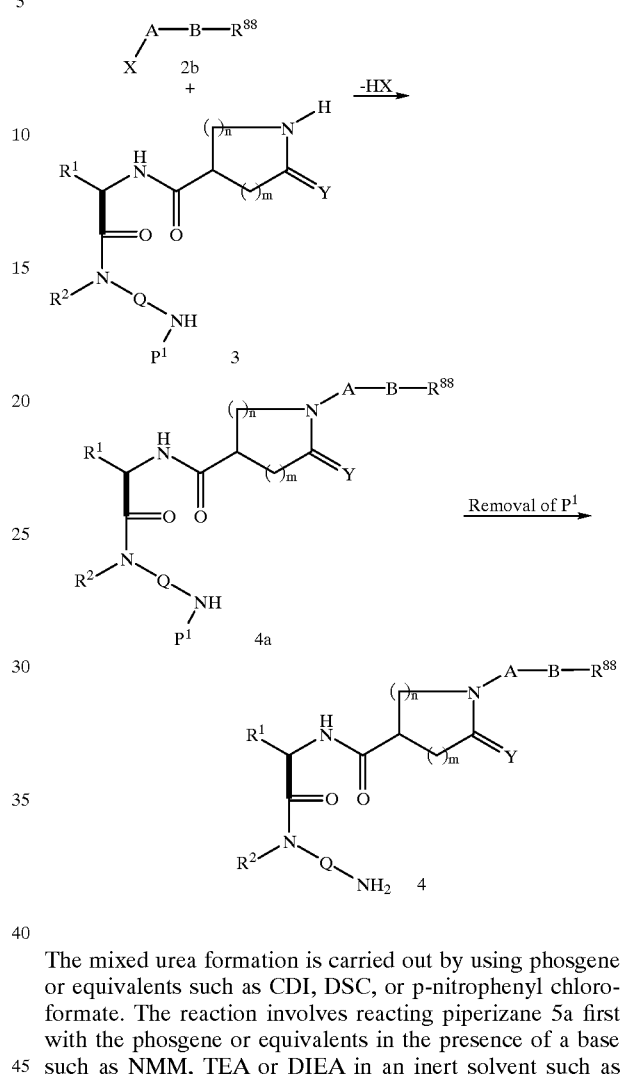

The mixed urea formation is carried out by using phosgene or equivalents such as CDI, DSC, or p-nitrophenyl chloroformate. The reaction involves reacting piperizane 5a first with the phosgene or equivalents in the presence of a base such as NMM, TEA or DIEA in an inert solvent such as DCM, THF and DMF or mixtures, followed by addition of the amine 1 and a base such as NMM, TEA or DIEA. Removal of protecting groups ($P^1$) is performed according to standard conditions.

Scheme 6

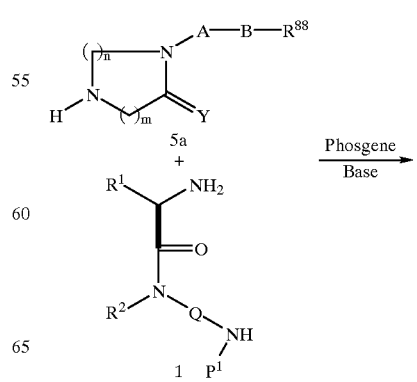

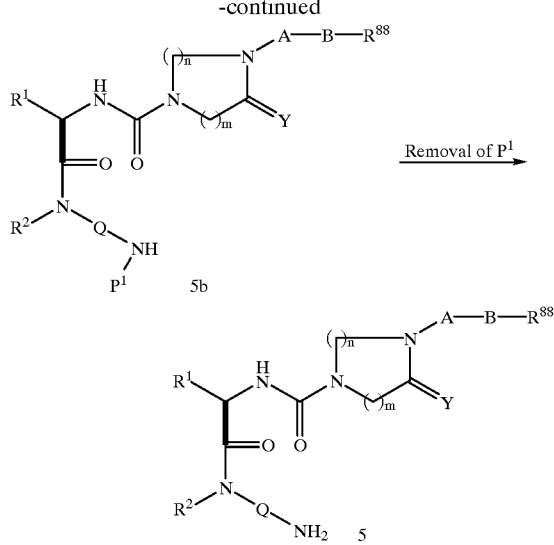

Many of the selective protected diamines 1a are either commercially available or known in the literature and others can be prepared following literature methods described for analogous compounds. Some of these methods are illustrated in subsequent schemes.

Cbz Protected diamine 11 was prepared from commercially available serinol oxalate 6 by standard Cbz protection to give 7, condensation with commercially available phthalimidylacetaldehyde, chromatographic separation of the cis/trans isomers 9 and 10, and hydrazinolysis of the phthalimide groups Monoprotected diamine 11 could be converted to its N-methylated analog 15 by conversion to its o-nitrophenylsulfonamide 13, methylation with methyl iodide giving 14, and cleavage of the sulfonamide using mercaptoacetic acid, followed by LiOH.H$_2$O.

General Procedure 1: Amide Formation from Acid and Amine

To a stirred solution of carboxylic acid (such as Intermediates 10–18), HOBT (1 equiv.) and the primary or secondary amine (such as Intermediates 3–5, 1.2 equiv.) in dichloromethane (final concentration at about 0.2 M) at 0° C. was added EDC (1.5 equiv.). If the amine is in its hydrochloride form, 1.2 equiv. of DIEA was added. The reaction mixture was stirred at 0° C. for 4 hours, and then poured in to 3 N HCl. The organic layer was subsequently washed with aqueous sodium bicarbonate and brine, dried and evaporated. Purification with silica chromatography give the desired product.

General Procedure 2: Hydrogenolysis Removal of Cbz

A mixture of the Cbz protected amine, 10% Palladium on carbon (5–10% weight of the Cbz compound) and 1 equiv. of HCl in ethanol is stirred under a hydrogen balloon for 2 h. The mixture is filtered through celite and evaporated to afford the amine salt.

General Procedure 3: Mixed Urea Formation

N-Monosubstituted piperizane was stirred first for 2 h with the phosgene (1.0 eq.) or equivalents in the presence of a base such as NMM, TEA or DIEA (1.0 eq.) in an inert solvent such as DCM, THF and DMF or mixtures, followed by addition of the amine 1 (1.0 eq.) and a base such as NMM, TEA or DIEA (1.0 eq.). Removal of protecting groups (P1) is performed according to standard conditions.

INTERMEDIATE 1

Step A:

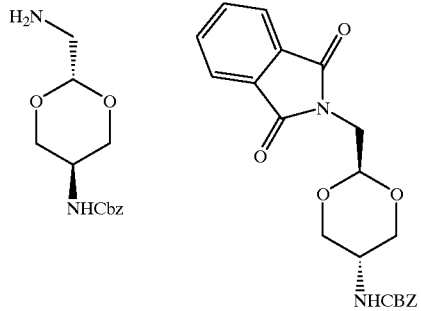

A stirred mixture of N-Cbz-serinol (497 mg, 2.21 mmol), (prepared using standard procedures from commercially available serinol oxalate and Cbz-Cl), phthalimidoacetaldehyde diethyl acetal (Aldrich, 581 mg, 2.21 mmol) and TsOH (21 mg, 0.11 mmol) in toluene (10 mL) was heated to reflux for 6 h. The resulting solution was cooled and evaporated in vacuo. Purification by flash chromatography (dry loaded on silica, 30% ethyl acetate/hexane to 40% ethyl acetate/hexane's) afforded a 4:1 trans/cis mixture (107 mg) and a 1:4 trans/cis mixture (300 mg). The trans isomer was crystallized from absolute ethanol.

Step B:

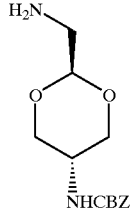

To a suspension of the product from the above reaction (106 mg, 0.268 mmol) in absolute ethanol was added hydrazine (1M solution in ethanol, 0.268 mmol) and the mixture was heated at reflux for 1 h. The resulting suspension was cooled and evaporated in vacuo. 2 M HCl (5 mL) was added and the mixture was warmed to 50° C. for 5 min. to give a suspension which was cooled and filtered. The solids were washed with more 2M HCl. The resulting solution was washed with DCM (2x) then basified with 50% NaOH solution (cooling in an ice bath), and the mixture was extracted with ethyl acetate (2x). The combined extracts were dried over Na₂SO₄, filtered and evaporated to give 57 mg of product as a waxy solid.

INTERMEDIATE 2

Step A:

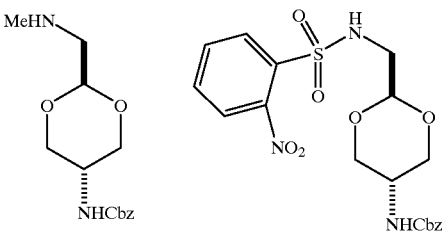

To a stirred solution of intermediate 1 (13.0 g, 48.9 mmol), triethylamine (8.18 mL, 5.94 g, 58.7 mmol), and catalytic DMAP (100 mg) in CH₂Cl₂ (150 mL) was added 2-nitrobenzenesulfonyl chloride (10.8 g, 48.9 mmol) in one portion. The reaction mixture was permitted to stir for 30 min, and was then washed with 3 N HCl, followed by brine. The organic layer was dried over MgSO₄, filtered and concentrated.

Step B:

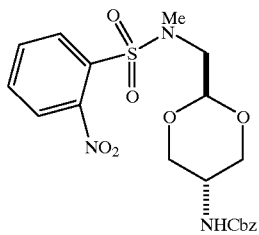

The crude product from step A above was dissolved in DMF (100 mL) and treated with K₂CO₃ (13.5 g, 97.8 mmol), followed by methyl iodide (3.96 mL, 9.03 g, 63.6 mmol). After 2 h at rt the reaction mixture was partioned between EtOAc and water. Work up in the usual fashion gave 18.7 g of product which was used as is in the following step.

Step C:

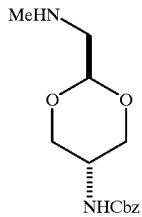

The product from step B above (16.7 g, 32.7 mmol) was dissolved in DMF (~75 mL) and treated with mercaptoacetic acid (6.02 g, 65.3 mmol), followed by LiOH•H₂O (5.48 g, 131 mmol). The reaction mixture was stirred overnight at rt, then partitioned between EtOAc and water. The aqueous phase was washed three times with EtOAc and the combined organic layers were subsequently washed three times with water and once with brine. The organic layer was dried over MgSO₄, filtered, and concentrated. Purification by flash chromatography (1:20:79 of NH₄OH/MeOH/CH₂Cl₂) afforded 5.38 g of product.

¹H NMR (CDCl₃, 400 Mhz) δ7.35–7.28 (m, 5H), 5.06 (s, 2H), 4.54–4.46 (m, 2H), 4.23–4.19 (m, 2H), 3.96–3.92 (m, 1H), 3.46–3.30 (m, 2H), 2.71 (d, J=4.8 Hz, 2H), 2.42 (s, 3H).

INTERMEDIATE 3

Step A:

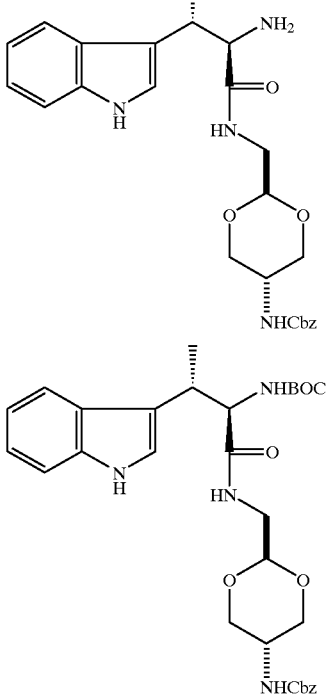

To a solution of (2R,3S)-N-BOC-β-methyl tryptophan (8.27 g, 26.0 mmol), intermediate 1 (6.92 g, 26.0 mmol), HOBt (5.27 g, 39.0 mmol) and DIEA (7.24 mL, 5.37 g, 41.6 mmol) in dichloromethane (~100 mL) at 0° C. was added EDC (7.47 g, 39.0 mmol) in portions over 5 min. The reaction mixture was allowed to warm to rt and stir for 3 h. The reaction mixture was diluted with CH₂Cl₂ and washed with 1 N HCl solution, saturated NaHCO₃ solution and brine. The organic layer was dried over MgSO₄, filtered and concentrated to provide 13.6 g of crude product.

Step B:

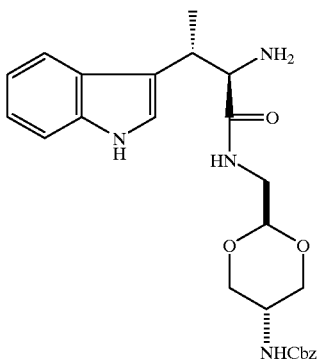

The product from step A above (2.38 g, 4.20 mmol) was dissolved in EtOAc and gaseous HCl was bubbled through the solution for ~3 min. The reaction mixture was concentrated to afford 2.15 g of product.

ESI-MS calc. for C₂₅H₃₀N₄O₅: 466; Found 467 (M+H).

INTERMEDIATE 4

Step A:

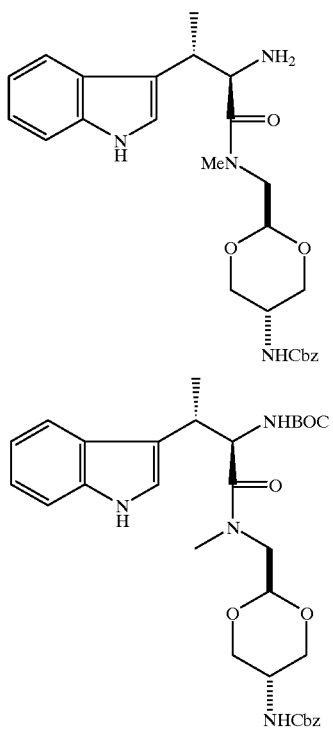

To a solution of (2R,3S)-N-BOC-β-methyl tryptophan (3.41 g, 10.7 mmol), intermediate 2 (3.00 g, 10.7 mmol), and DIEA (4.15 g, 32.1 mmol) in CH₂Cl₂ (100 mL) was added PyBroP (5.74 g, 12.3 mmol) and the resulting mixture was stirred at rt overnight. The reaction mixture was washed twice with water, then with saturated NaHCO₃ solution, and brine. The organic phase was dried over MgSO₄, filtered and concentrated. Purification by flash chromatography (50% EtOAc/hexanes) afforded 4.80 g of coupled product (77% yield).

ESI-MS calc. for C₃₁H₄₀N4O₇: 580; Found 581 (M+H).

Step B:

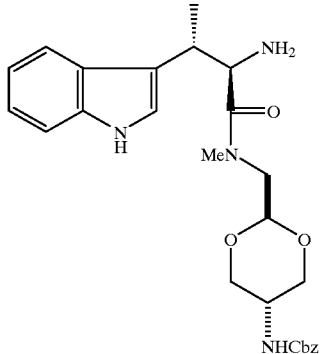

The BOC intermediate from step A above (3.30 g, 5.69 mmol) was treated with neat TFA (30 mL) and stirred for 1.5 h. The reaction mixture was diluted with CH₂Cl₂ and treated with concentrated aqueous NH₄OH solution until the pH reached ~11. Water was added, the phases were separated, and the organic layer was further washed with brine, dried over MgSO₄, filtered and concentrated to give 2.80 g of product.

INTERMEDIATE 5

Step A:

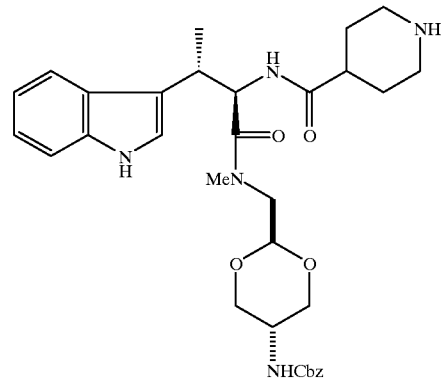

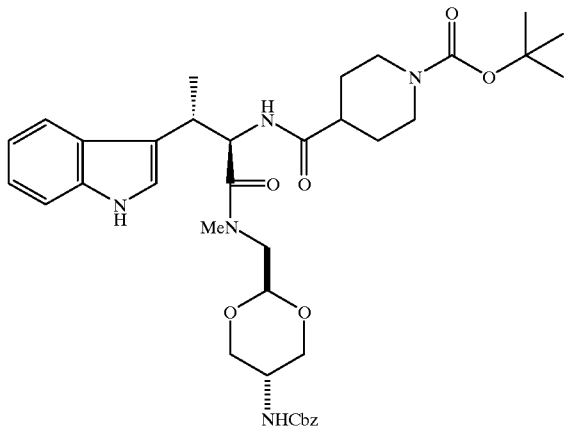

To a solution of N-BOC-iso-nipecotic acid (1.37 g, 6.0 mmol), intermediate 4 (2.90 g, 10.7 mmol) and HOBt (0.811 g, 6.0 mmol) in CH₂Cl₂ (200 mL) was added EDC (1.15 g, 6.0 mmol) in one portion. The resulting mixture was stirred at rt for 2 h. The reaction mixture was washed twice with water, then with saturated NaHCO₃ solution, and brine. The organic phase was dried over MgSO₄, filtered and concentrated. Purification by MPLC(EtOAc) afforded 3.0 g of coupled product (87% yield).

ESI-MS calc. for C₃₇H₄₉N₅O₈: 691; Found 692 (M+H).

Step B:

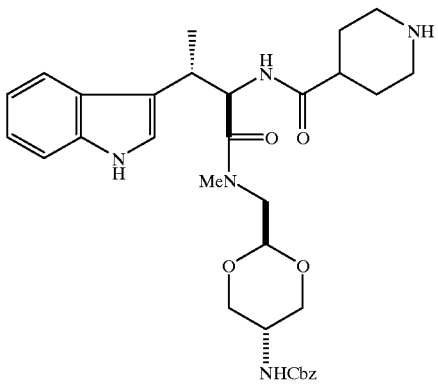

The BOC intermediate from step A above (2.90 g, 4.2 mmol) was treated with 4N HCl/dioxane(20 mL, 80 mmol) and stirred for 0.5 h. The reaction mixture was poured into sat. aq. NaHCO₃ (300 mL), extracted with EtOAc (2×200 mL). The combined organic phases were washed with water and brine, dried over MgSO₄, filtered and concentrated to give 2.20 g of product.

ESI-MS calc. for C₃₂H₄₁N5O₆: 591; Found 592 (M+H).

INTERMEDIATE 6

Step A:

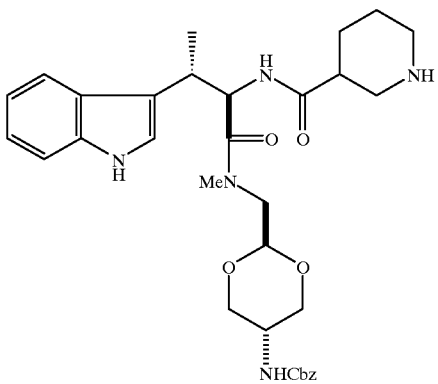

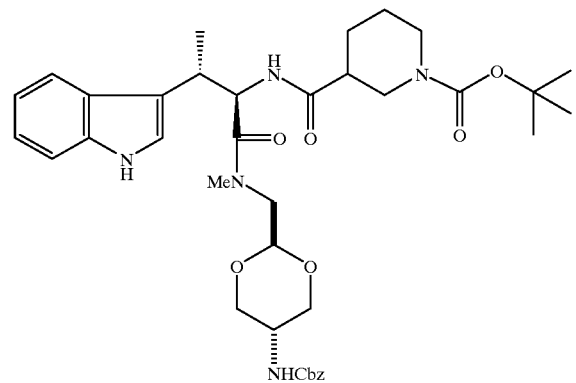

To a solution of N-BOC-nipecotic Acid (0.505 g, 2.2 mmol), intermediate 4 (1.16 g, 2.0 mmol), HOBt (0.297 g, 2.2 mmol) and DIEA (0.65 g, 5.0 mmol) in CH$_2$Cl$_2$ (25 mL) was added PyBOP(1.15 g, 2.21 mmol) in five portions in 10 min. The resulting mixture was stirred at rt for 2 h. The reaction mixture was washed twice with water, then with saturated NaHCO$_3$ solution, and brine. The organic phase was dried over MgSO$_4$, filtered and concentrated. Purification by MPLC (80%EtOAc/Hexane) afforded the desired product (0.6922 g, 50% yield).

ESI-MS calc. for C$_{37}$H$_{49}$5O$_8$: 691; Found 692 (M+H).

Step B:

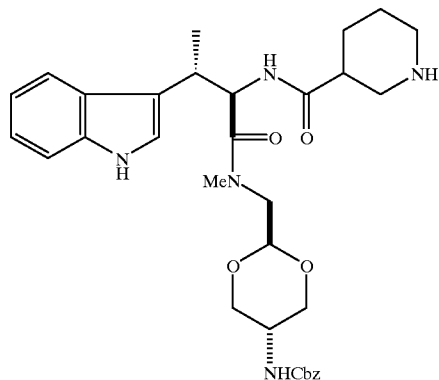

The BOC intermediate from step A above (0.692 g, 1.0 mmol) was treated with 4N HCl/dioxane(10 mL, 40 mmol) and stirred for 0.5 h. The reaction mixture was poured into sat. aq. NaHCO$_3$ (100 mL), extracted with EtOAc (2×100 mL). The combined organic phases were washed with water and brine, dried over MgSO$_4$, filtered and concentrated to give 0.42 g of product.

ESI-MS calc. for C$_{32}$H$_{41}$N5O$_6$: 591; Found 592 (M+H).

INTERMEDIATE 7

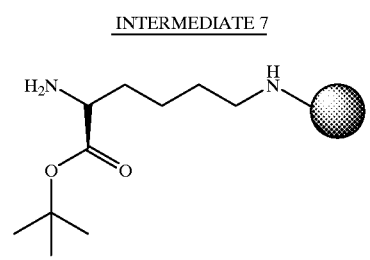

Lysine-t-butyl ester (5.5 g, 27 mmol) was combined with DIEA (2.6 mL, 1.95, 15.0 mmol) and Cl-2-Cl-trityl resin (1 mmol/g, 6.5 g, 6.5 mmol) in CH$_2$Cl$_2$ (50 mL). After stirring at rt for three days the mixture was diluted with methanol and filtered. The resin was further washed with CH$_2$Cl$_2$(5× 50 mL), MeOH (2×50 mL), CH$_2$Cl$_2$ (2×50 mL) and ether (2×50 mL), dried over N$_2$ flow.

INTERMEDIATE 8

Step A:

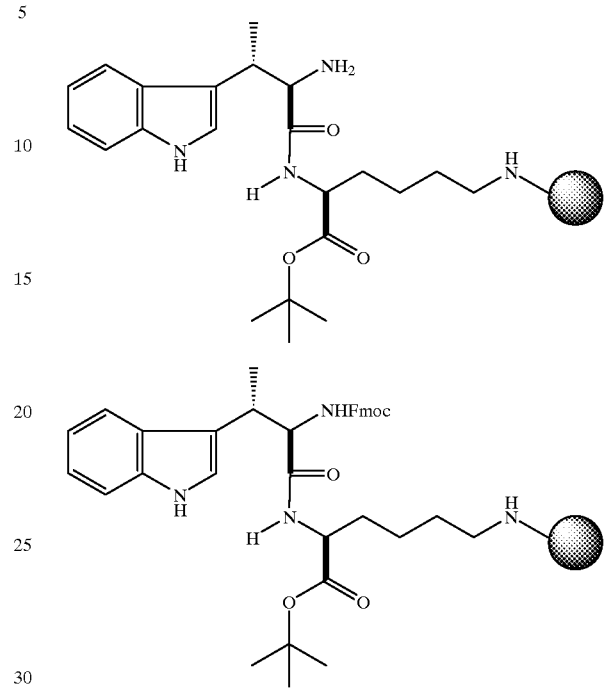

To a stirred mixture of (2R,3S)-N-Fmoc-β-methyl tryptophan N-(4.4 g, 1 mmol),intermediate 7 (5.0 g, ~5.0 mmol), HOBt (1.35 g, 10 mmol) and DIEA (3.6 mL, 20 mmol) in DMF (50 mL) at 0° C. was added PyBOP(5.2 g, 10 mmol) in five portions in 10 min. The resulting mixture was stirred at rt for 3 h. Kaiser test was negative. The resin was filtered, washed with DMF (5×50 mL) and used for Step B.

Step B:

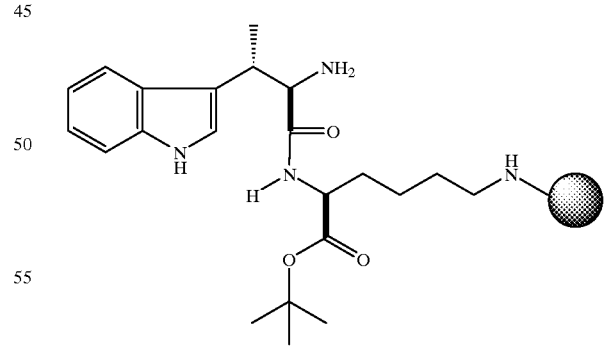

The FMOC intermediate from step A above was washed with 25% piperidine in DMF (2×50 mL), stirred with 50 mL of 25% piperidine in DMF for 45 min, filtered, washed with DMF (3×50 mL), THF (3×50 mL), DCM (3×50 mL), ether (2×50 mL) and dried over N$_2$ flow for 5 h.

INTERMEDIATE 9

Step A:

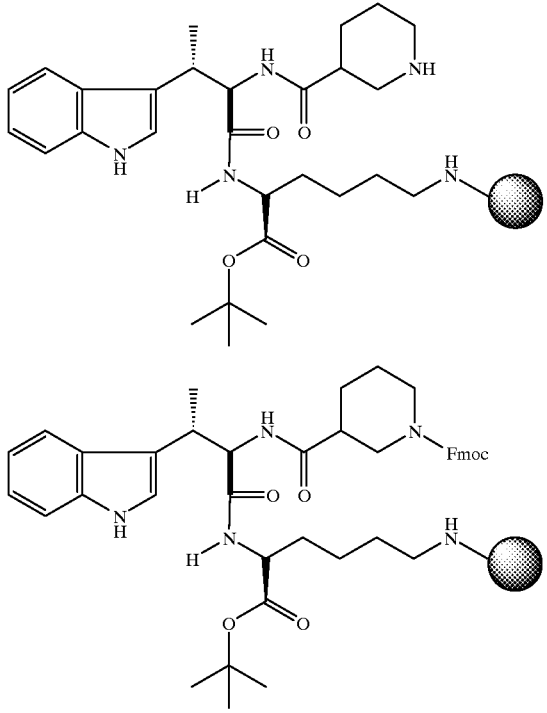

To a stirred mixture of N-Fmoc-iso-nipecotic acid (2.10 g, 6.0 mmol), intermediate 8 (3.0 g, 3.0 mmol), HOBt (0.81 g, 6.0 mmol) and DIEA (1.55 g, 12.0 mmol) in DMF (30 mL) at 0° C. was added PyBOP(3.12 g, 6.0 mmol) in five portions in 5 min. The resulting mixture was stirred at 0° C. for 3 h. Kaiser test was negative. The resin was filtered, washed with DMF (5×50 mL) and used for Step B.

Step B:

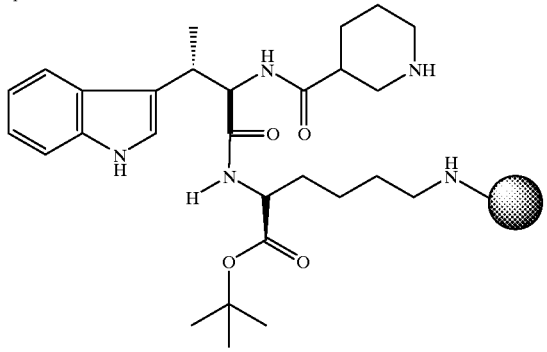

The FMOC intermediate from step A above was washed with 25% piperidine in DMF (2×30 mL), stirred with 40 mL of 25% piperidine in DMF for 45 min, filtered, washed with DMF (3×50 mL), THF (3×50 mL), DCM (3×50 mL), ether (2×50 mL) and dried over $N_2$ flow.

INTERMEDIATE 10

Step A:

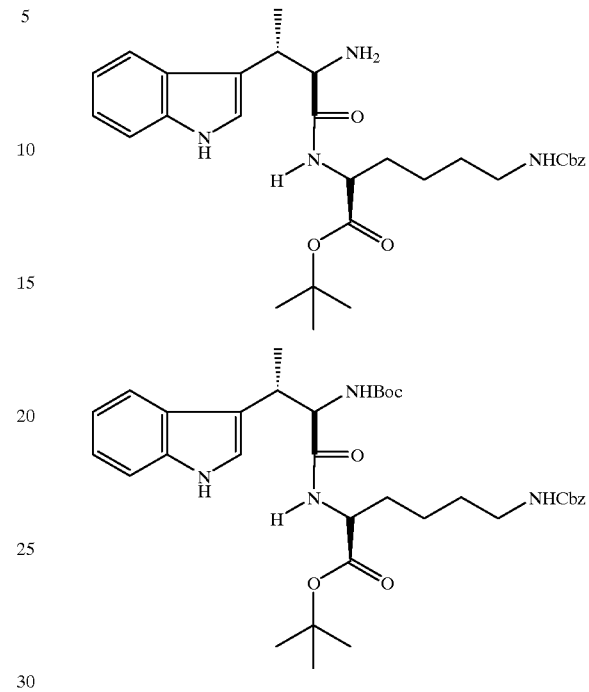

To a solution of (2R,3S)-N-BOC-β-methyl tryptophan (7.79 g, 24.5 mmol), N-ε-Cbz-L-lysine t-butyl ester hydrochloride (10.04 g, 26.9 mmol), HOBt (4.96 g, 36.7 mmol) and DIEA (4.69 mL, 26.9 mmol) in DCM (150 mL) at 0° C. was added EDC (7.04 g, 36.7 mmol) in portions over a period of 10 min. The reaction mixture was allowed to warm to room temperature, stirred for 3.75 h, and poured into a saturated solution of $NaHCO_3$ (100 mL). The organic layer was separated and washed sequentially with 1N aq. HCl (100 mL), water (100 mL), and brine (100 mL), then dried over anhydrous $MgSO_4$, filtered and concentrated to give 14.5 g (93% crude yield) of a white/yellow solid.

ESI-MS calc. for $C_{35}H_{48}N_4O_7$: 636; Found 637 (M+H).

Step B:

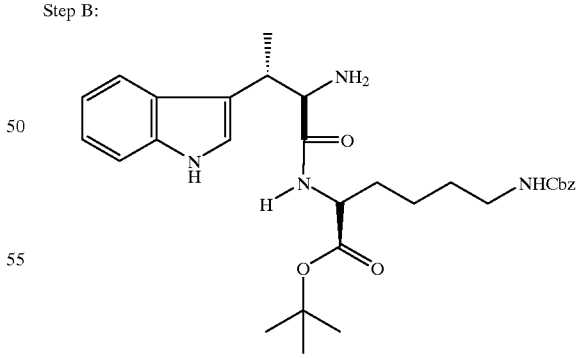

To a solution of the above adduct (554 mg, 0.870 mmol) in methanol (8 mL) was added methane sulfonic acid (251 mg, 2.61 mmol) and the resulting mixture was stirred at room temperature for 70 h. The reaction mixture was concentrated to remove the methanol, dissolved in DCM (50 mL) and washed three times with 2N NaOH solution (40 mL), once with brine (40 mL) and dried over anhydrous Na$_2$SO$_4$, filtered and concentrated to give 280.1 mg (60% yield) of a white solid. HPLC analysis indicated 93% purity of the desired amine.

ESI-Mass cacl. for C$_{30}$H$_{40}$N$_4$O$_5$: 536; Found 537 (M+H).

INTERMEDIATE 11

Step A:

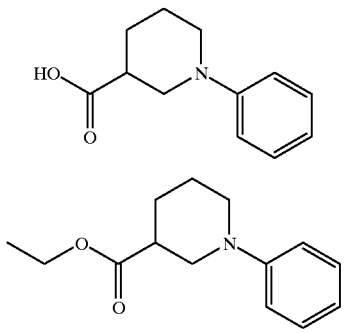

Ethyl nipecotate (3.46 g, 22 mmol), bromobenzene (3.14 g, 20 mmol), sodium tert-butoxide (2.7 g, 28 mmol), BINAP (0.0934 g, 0.15 mmol), Pd$_2$(dba)$_3$ (0.0458 g, 0.05 mmol) and dioxane (50 mL) were combined in a 100 mL flask in an oil bath. The flask were stirred, purged and protected with Ar flow. The temperature of the oil bath was raised to 80° C. The mixture was stirred for 4 h, concentrated to remove dioxane, diluted with DCM, worked up with water and brine, dried over Na$_2$SO$_4$ and evaporated. The residue was purified by FC (20%EtOAc/Hexane) to afford a brown oil (3.4 g, 14.6 mmol, yield: 66%).

Step B:

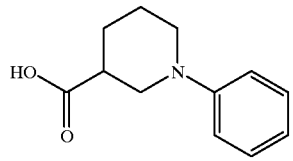

The ester (0.5 g, 0.21 mmol) was stirred with LiOH•H$_2$O (0.418 g, 10 mmol), MeOH (10 mL) and H$_2$O (5 mL) at rt overnight. The pH of the mixture was adjusted to ~2–3 by addition of 3N HCl and the resulting solution was extracted with ethyl acetate 3 times. The combined organic layers were washed with brine, dried over Na$_2$SO$_4$, filtered and concentrated to give the acid (0.21 g, 1.0 mmol, yield: 47.6%).

INTERMEDIATE 12

Step A:

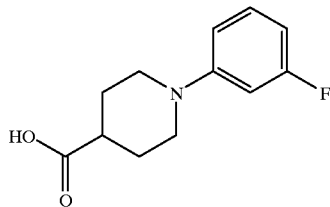

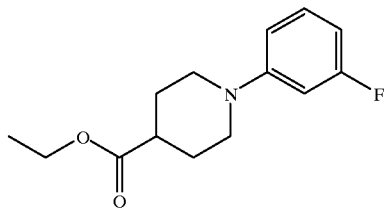

Ethyl nipecotate (1.89 g, 12 mmol), 1-bromo-3-fluorobenzene (2.0 g, 11.43 mmol), sodium tert-butoxide (1.65 g, 17.15 mmol), BINAP (0.072 g, 0.1143 mmol), Pd$_2$(dba)$_3$ (0.053 g, 0.057 mmol) and dioxane (50 mL) were combined in a 100 mL flask in an oil bath. The flask were stirred, purged and protected with Ar flow. The temperature of the oil bath was raised to 80° C. The mixture was stirred for 4 h, concentrated to remove dioxane, diluted with DCM, worked up with water and brine, dried over Na$_2$SO$_4$ and evaporated. The residue was purified by FC (10%EtOAc/Hexane) to afford a brown oil (0.43 g, 1.72 mmol, yield: 14%).

Step B:

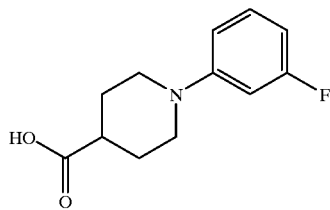

The ester (0.43 g, 1.72 mmol) was stirred with LiOH•H$_2$O (0.418 g, 10 mmol), MeOH (10 mL) and H$_2$O (5 mL) at rt overnight. The pH of the mixture was adjusted to ~2–3 by addition of 3N aq. HCl and the resulting solution was extracted with ethyl acetate 3 times. The combined organic layers were washed with brine, dried over Na$_2$SO$_4$, filtered and concentrated to give the acid (0.283 g, 0.805 mmol, yield: 47%).

INTERMEDIATE 13

Step A:

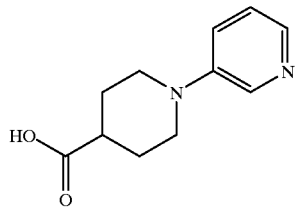

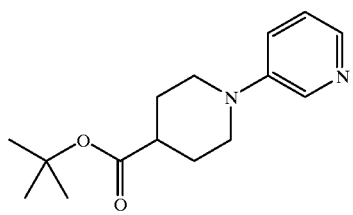

Ethyl nipecotate (2.0 g, 8.48 mmol), 3-bromopyridine (2.11 g, 8.91 mmol), sodium tert-butoxide (1.84 g, 12.72 mmol), BINAP (0.083 g, 0.0891 mmol), Pd$_2$(dba)$_3$ (0.062 g, 0.0445 mmol) and dioxane (50 mL) were combined in a 100 mL flask in an oil bath. The flask were stirred, purged and protected with Ar flow. The temperature of the oil bath was raised to 86° C. The mixture was stirred overnight, concentrated to remove dioxane, diluted with DCM, worked up with water and brine, dried over Na$_2$SO$_4$ and evaporated. The residue was purified by FC (80%EtOAc/Hexane) to afford two components: less polar t-butyl ester (0.358 g, 1.37 mmol, yield: 16%) and more polar ethyl ester (0.242 g).

Step B:

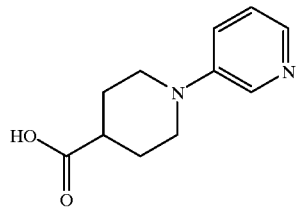

The t-butyl ester (0.5 g, 0.21 mmol) was refluxed with 4N HCl/dioxane solution overnight, evaporated to afford a solid residue which was directly used for further coupling.

INTERMEDIATE 14

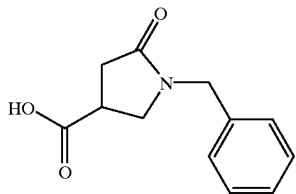

The commercially available (Aldrich) methyl ester (0.83 g, 3.56 mmol) was stirred with LiOH•H$_2$O (0.856 g, 20 mmol), MeOH (10 mL) and H$_2$O (5 mL) at rt overnight. The pH was adjusted to ~2–3 by addition of 3N HCl and the resulting solution was extracted with ethyl acetate 3 times. The combined organic layers were washed with brine, dried over Na$_2$SO$_4$, filtered and concentrated to give the acid (0.52 g, 2.37 mmol, yield: 67%).

INTERMEDIATE 15

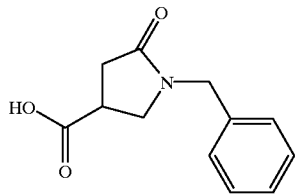

The corresponding N-para-chlorophenyl congener was commercially available from Sailor. It could be directly used for further coupling and the chloro atom and Cbz protecting group on the coupling product then simultaneously removed by hydrogenolysis using 10% Pd(OH)$_2$/carbon (5–10% weight of the chlorophenyl compound) as catalyst and methanol as solvent under a hydrogen balloon for 2 h.

INTERMEDIATE 16

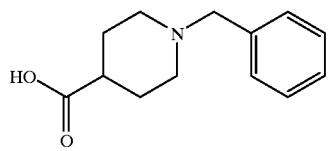

Step A:

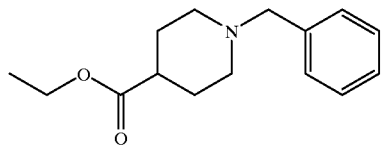

A mixture of ethyl iso-nipecotate (7.85 g, 50 mmol), benzyl bromide(8.55 g, 50 mmol), DIEA (6.46 g, 50 mmol) and DCM (200 mL) was heated at 60° C. for 2 h, cooled, washed thoroughly with water, dried over Na$_2$SO$_4$, evaporated to afford an oil (10.5 g, yield=85 %).

Step B:

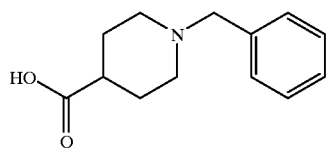

A mixture of the above ester (10 g, 40.46 mmol), NaOH (4.86 g, 121 mmol) in water (50 mL) and EtOH (50 mL) was stirred at rt for 2 h. EtOH was removed by evaporation. The pH was adjusted to ~6–7 by addition of 3N aq. HCl and no precipitate formed. Evaporated to dryness, dissolved in MeOH, filtered off solid (NaCl), evaporated to give the crude acid.

INTERMEDIATE 17

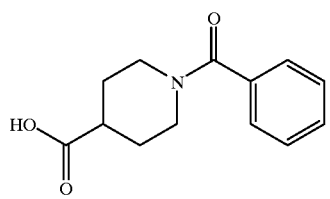

Step A:

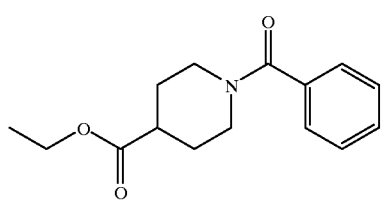

To a stirred solution of ethyl iso-nipecotate (5.0 g, 31.80 mmol), DIEA (4.43 mL, 31.80 mmol) in DCM (50 mL) was added dropwise benzoyl chloride (1.0 eq.) at rt, the resulting mixture was stirred for 30 min. The organic phase was washed with water, 1N aq. HCl and brine, dried over Na$_2$SO$_4$ and evaporated to afford an oil (7.5 g, yield: 90%).

Step B:

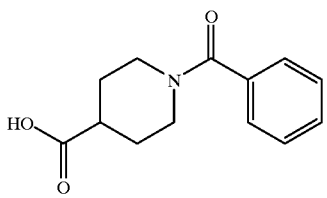

The above ester (7.0 g, 26.72 mmol) was stirred with LiOH•H$_2$O (5.65 g, 134.62 mmol) in THF/MeOH/Water (40 mL/40 mL/40 mL) overnight. The pH was adjusted to ~2–3 by addition of 3N aq. HCl and the resulting solution was extracted with ethyl acetate 3 times. The combined organic layers were washed with brine, dried over Na$_2$SO$_4$, filtered and concentrated to give the acid.

INTERMEDIATE 18

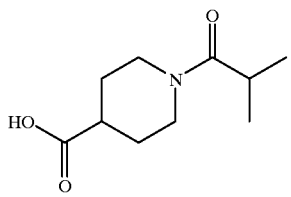

Step A:

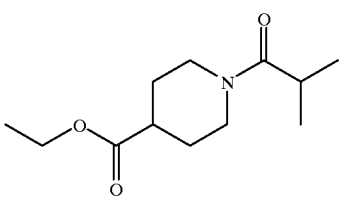

To a stirred solution of ethyl iso-nipecotate (5.0 g, 31.80 mmol), DIEA (4.43 mL, 31.80 mmol) in DCM (50 mL) was added dropwise isobutyryl chloride at rt, the resulting mixture was stirred for 30 min. The organic phase was washed with water, 1N aq. HCl and brine, dried over Na$_2$SO$_4$ and evaporated to afford an oil (7.12 g, yield: 97%).

Step B:

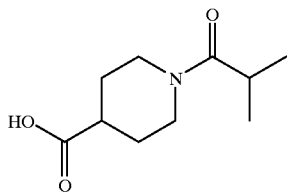

The above ester (6.12 g, 26.72 mmol) was stirred with LiOH•H$_2$O (5.65 g, 134.62 mmol) in THF/MeOH/Water (40 mL/40 mL/140 mL) overnight. The pH was adjusted to ~2–3 by addition of 3N aq. HCl and the resulting solution was extracted with ethyl acetate 3 times. The combined organic layers were washed with brine, dried over Na$_2$SO$_4$, filtered and concentrated to give the acid.

INTERMEDIATE 19

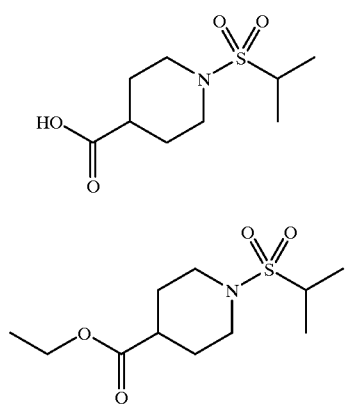

Step A:

To a stirred solution of ethyl iso-nipecotate (5.0 g, 31.80 mmol), DIEA (4.43 mL, 31.80 mmol) in DCM (50 mL) was added dropwise isopropylsulfonyl chloride at rt, the resulting mixture was stirred for 30 min. The organic phase was washed with water, 1N aq. HCl and brine, dried over Na$_2$SO$_4$ and evaporated to afford an oil (7.22 g, yield: 86%).

Step B:

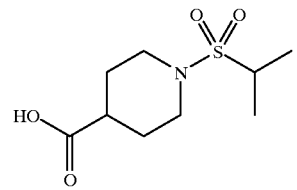

The above ester (6.22 g, 23.62 mmol) was stirred with LiOH•H$_2$O (4.96 g, 118.09 mmol) in THF/MeOH/Water (40 mL/40 mL/40 mL) overnight. The pH was adjusted to ~2–3 by addition of 3N aq. HCl and the resulting solution was extracted with ethyl acetate 3 times. The combined organic layers were washed with brine, dried over Na$_2$SO$_4$, filtered and concentrated to give the acid.

The following Examples are provided to illustrate the invention and are not to be construed as limiting the scope of the invention in any way.

EXAMPLE 1

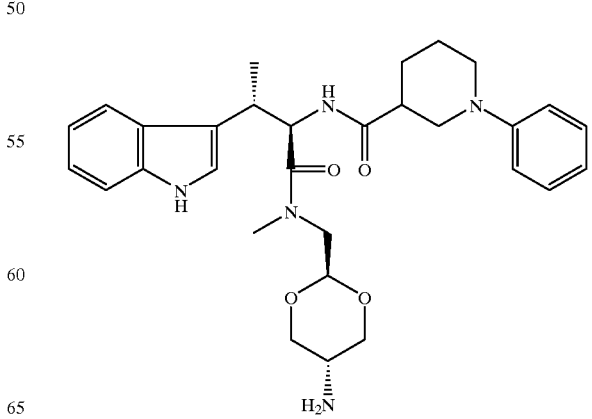

The title compounds as HCl salts (two isomers: 220 mg+220 mg) were prepared by coupling Intermediate 4 (480 mg, 1.0 mmol) and Intermediate 10 (210 mg, 1.0 mmol) according to the general procedure 1. The resulting two diasteromers were separated by MPLC (90%EtOAc/Hexane) and then subjected to the general procedure 2 to remove the Cbz protecting groups.

ESI-MS calc. for C30H39N5O4: 533; Found 534(M+H).

EXAMPLE 2

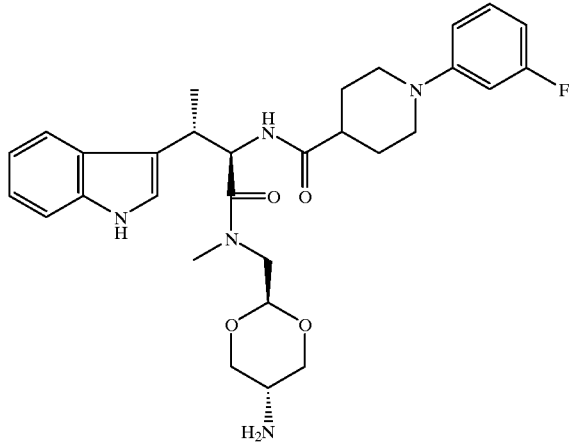

The title compound as a HCl salt (190 mg, 0.34 mmol) was prepared by a procedure similar to the Example 1 starting with Intermediates 4 and 12.

ESI-MS calc. for C30H38FN5O4: 551; Found 552(M+H).

EXAMPLE 3

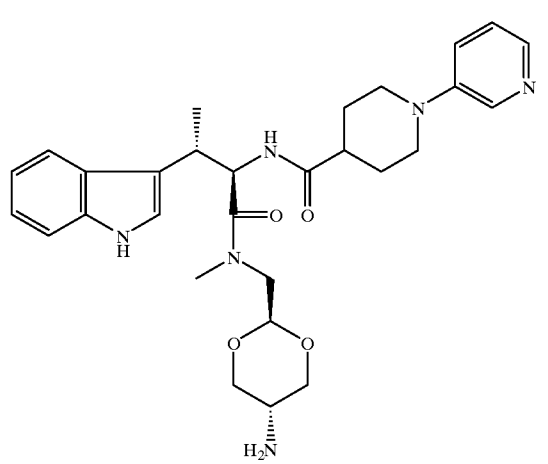

The title compound as a HCl salt (167 mg, 0.312 mmol) was prepared by a procedure similar to the Example 1 starting with Intermediates 4 and 13.

ESI-MS calc. for C29H38N6O4: 535; Found 535(M+H).

EXAMPLE 4

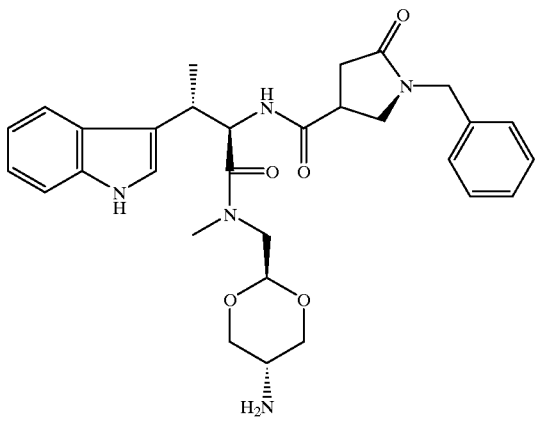

The title compounds as HCl salts (two diasteromers: 52 mg+50 mg) were prepared by a procedure similar to the Example 1 starting with Intermediates 4 and 14.

ESI-MS calc. for C30H37N5O5: 547; Found 548(M+H).

EXAMPLE 5

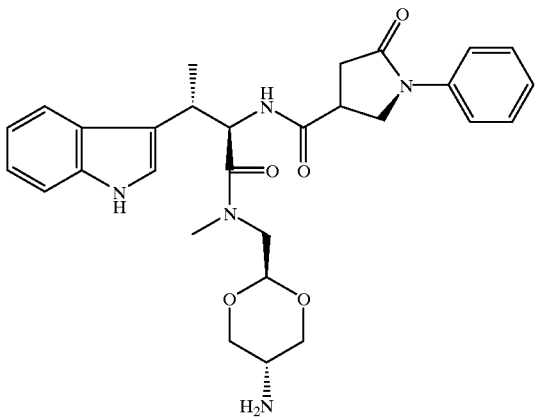

The title compounds as HCl salts (two diasteromers: 120mg+100 mg) was prepared by a procedure similar to the Example 1 starting with Intermediates 4 and 15.

ESI-MS calc. for C29H35N5O5: 534; Found 535(M+H).

EXAMPLE 6

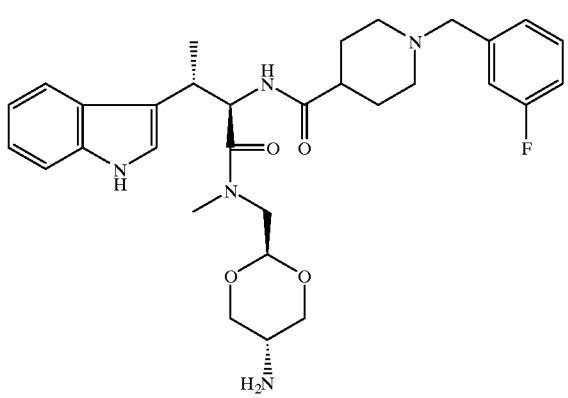

To a stirred solution of Intermediate 5 (200 mg, 0.338 mmol), 3-fluorobenzaldehyde (60 mg, 0.5 mmol) and NaCNBH$_3$ (60 mg, 0.67 mmol) in MeOH (2 mL) was added a dop of acetic acid with a pipette. The resulting mixture was stirred for 3 h, evaporated, dissolved in water, extracted with ethyl acetate, dried over MgSO$_4$, filtered and evaporated. The residue was purified by preparative TLC (10%MeOH/EtOAc) to give the desired product as an oil (130 mg). The title compound as a HCl salt (104 mg) was obtained after removal of Cbz according to the general procedure 2.

ESI-MS calc. for C31H40FN5O4: 565; Found 566(M+H).

EXAMPLE 7

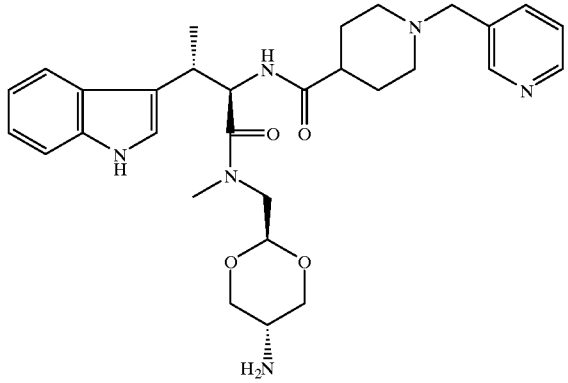

The title compound as a HCl salt (70 mg) was prepared by a procedure similar to the Example 6 starting with Intermediate 5 and 3-pyridylcarboxaldehyde.

ESI-MS calc. for C30H40FN6O4: 548; Found 549(M+H).

EXAMPLE 8

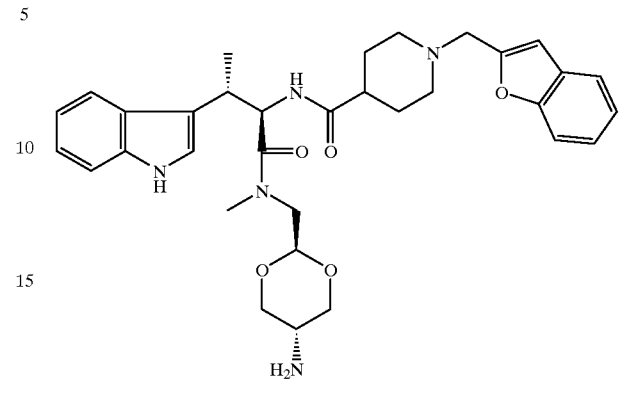

The title compound as a HCl salt (120 mg) was prepared by a procedure similar to the Example 6 starting with Intermediate 5 and 2-benzo[b]furan-carboxaldehyde.

ESI-MS calc. for C33H41FN5O5: 587; Found 588(M+H).

EXAMPLE 9

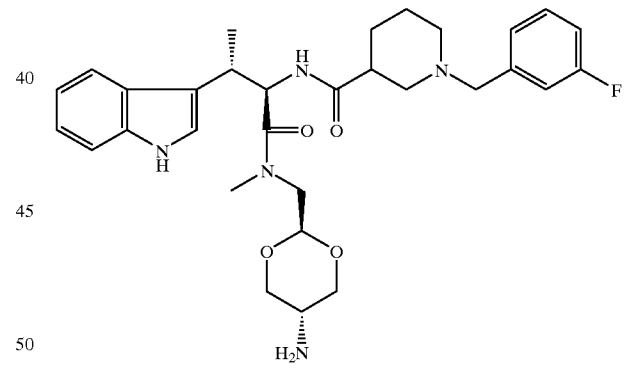

A mixture of Intermediate 6 (120 mg, 0.2 mmol), 3-fluorobenzylbromide (76 mg, 0.4 mmol), DIEA (129 mg, 1.0 mmol) and DCM (5 mL) was heated at 60° C. for 30 min, worked up with water and brine, dried and filtered, concentrated, purified by MPLC (10%MeOH/EtOAc) to give the desired product as an oil (107 mg). The title compounds (52+52 mg) as HCl salts were obtained after removal of Cbz according to the General procedure 2.

ESI-MS calc. for C31H40FN5O4: 565; Found 566(M+H).

EXAMPLE 10

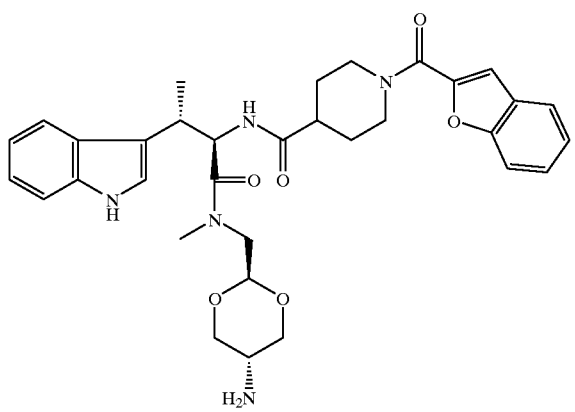

A mixture of Intermediate 5 (200 mg, 0.338 mmol), 2-benzofurancarboxylic acid (67 mg, 0.41 mmol), HOBt (55 mg, 0.41 mmol) and EDC(78 mg, 0.41 mmol) in DCM (5 mL) was stirred for 2 h., worked up with water and brine, dried and filtered, concentrated, purified by MPLC (10%MeOH/EtOAc) to give the desired product as an oil (140 mg, yield=56%). The title compound (95 mg) as a HCl salt was obtained after removal Cbz according to the General procedure 2.

ESI-MS calc. for C33H39FN5O6: 601; Found 602(M+H).

EXAMPLE 11

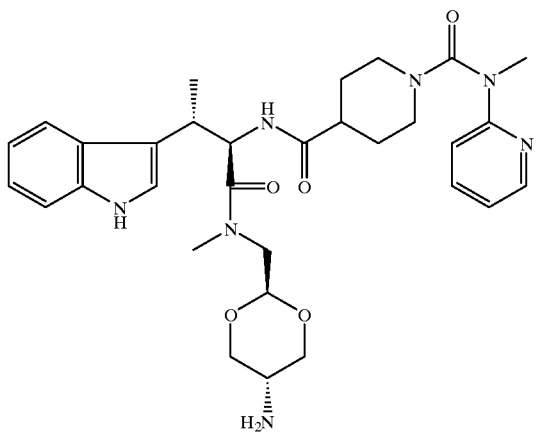

To a solution of 2-methylaminopyridine (37 mg, 0.338 mmol) and DIEA (87 mg, 0.676 mmol) in DCM (5 mL) was added solid 4-nitrophenoxylcarbonyl chloride (68 mg, 0.338 mmol). The resulting solution was stirred for 30 min and then Intermediate 4 (200 mg, 0.338 mmol) was added, stirred for 3 h. The reaction was worked up with sat. aq. NaHCO3, dried with Na2SO4, evaporated and purified by MPLC (10%MeOH/EtOAc) to afford the desired product (120 mg). The title compound (92 mg) as a HCl salt was obtained after removal of Cbz according to the General procedure 2.

ESI-MS calc. for C31H41FN7O5: 591; Found 592(M+H).

EXAMPLE 12

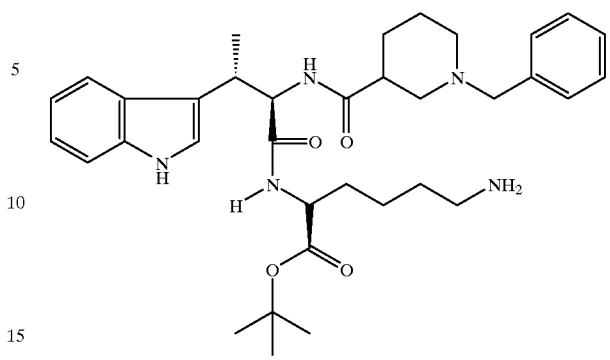

A mixture of Intermediate 9 resin (50 mg, 0.05 mmol), DIEA (65 mg, 0.5 mmol), benzyl bromide (43 mg, 0.25 mmol) and DCM (2 mL) in a capped vial was heated at 60° C. for 3 h. The resin was filtered, washed with DCM (3×5 mL), MeOH (2×5 mL), DCM (3×5 mL) and ether (2×5 mL). After dried over N2 flow, the resin was heated at 40° C. with 2.0 mL of acetic acid in a capped vial overnight, filtered, washed with acetic acid (2×2 mL). The filtrates were combined and lyophilized to give the title compound as acetic acid salt (15 mg).

ESI-MS calc. for C35H49N5O4: 603; Found 604(M+H).

Similarly the following additional examples are prepared using commercially available alkyl halides and Intermediate 9 according to the same procedure shown in the preparation of example 12.

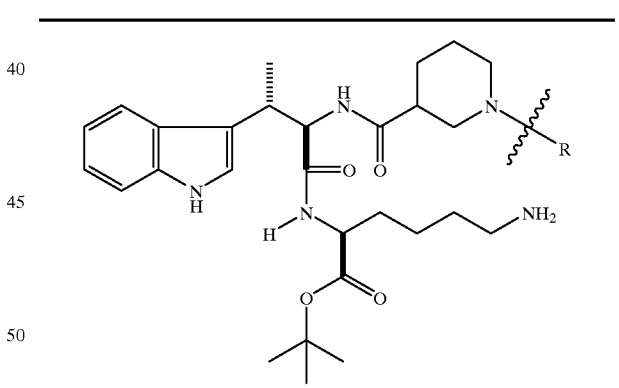

| Entry | R | ESI-MS (M + 1) |
|---|---|---|
| 1 | 3-fluorobenzyl | 622 |
| 2 | 3,4-difluorobenzyl | 640 |

-continued

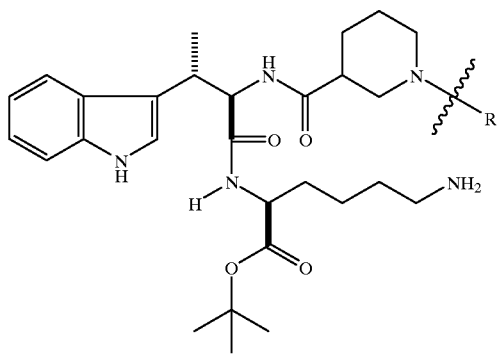

| Entry | R | ESI-MS (M + 1) |
|---|---|---|
| 3 | 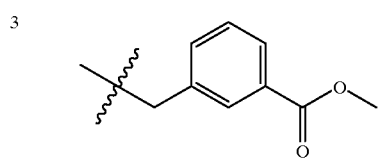 | 662 |
| 4 | 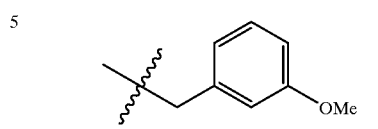 | 680 |
| 5 | 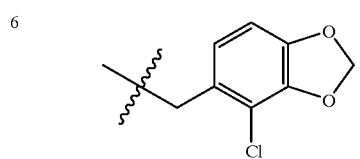 | 634 |
| 6 | 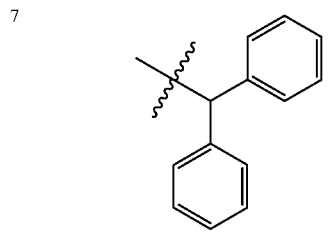 | 682 |
| 7 | 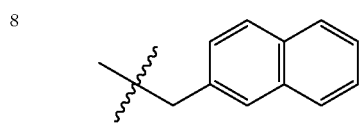 | 680 |
| 8 | | 654 |

-continued

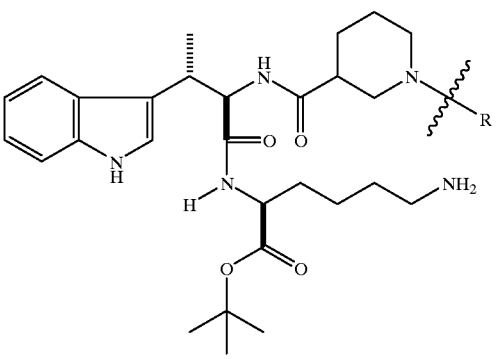

| Entry | R | ESI-MS (M + 1) |
|---|---|---|
| 9 | 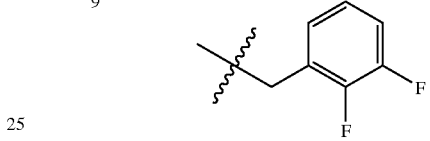 | 640 |

EXAMPLE 13

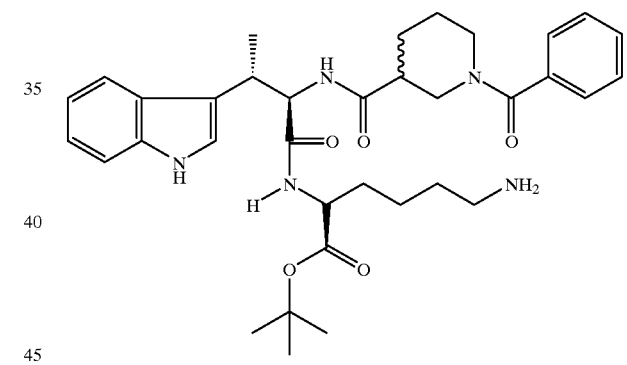

A mixture of Intermediate 9 (50 mg, 0.05 mmol), DIEA (65 mg, 0.5 mmol), benzoic acid (31 mg, 0.25 mmol), HOBt (34 mg, 0.25 mmol), PyBOP (130 mg, 0.25 mmol) and DCM (2 mL) in a capped vial was shaken for 3 h. The resin was filtered, washed with DCM (3×5 mL), MeOH (2×5 mL), DCM (3×5 mL) and ether (2×5 mL). After dried over $N_2$ flow, the resin was heated at 40° C. with 2.0 mL of acetic acid in a capped vial overnight, filtered, washed with acetic acid (2×2 mL). The filtrates were combined and lyophilized to give the title compound as acetic acid salt (13 mg).

ESI-MS calc. for C35H47N5O4: 617; Found 618(M+H).

Similarly the following additional examples are prepared using commercially available acid and Intermediate 9 according to the same procedure shown in the preparation of example 13.

| Entry | R | ESI-MS (M + 1) |
|---|---|---|
| 1 | [1,3-benzodioxol-5-yl] | 662 |
| 2 | [pyridin-3-yl] | 619 |
| 3 | [benzimidazol-5-yl] | 658 |
| 4 | [3-acetamidophenyl] | 675 |
| 5 | [1,3-benzodioxol-5-ylmethyl] | 676 |
| 6 | [3,5-difluorophenyl-CH-] | 668 |
| 7 | [diphenylmethyl] | 708 |
| 8 | [1,1-diphenyl-1-hydroxyethyl] | 724 |
| 9 | [isobutyl-CH(CH3)-] | 598 |

EXAMPLE 14

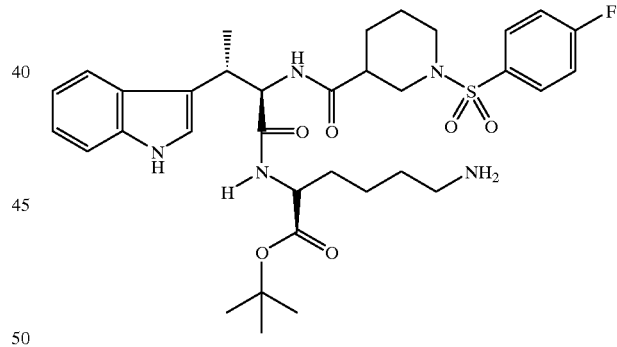

A mixture of Intermediate 9 (50 mg, 0.05 mmol), DIEA (65 mg, 0.5 mmol), 3-fluorobenzenesulfonyl chloride (19 mg, 0.25 mmol) and DCM (2 mL) in a capped vial was shaken for 3 h. The resin was filtered, washed with DCM (3×5 mL), MeOH (2×5 mL), DCM (3×5 mL) and ether (2×5 mL). After dried over $N_2$ flow, the resin was heated at 40° C. with 2.0 mL of acetic acid in a capped vial overnight, filtered, washed with acetic acid (2×2 mL). The filtrates were combined and lyophilized to give the title compound as acetic acid salt (13 mg).

ESI-MS calc. for $C_{34}H_{46}FN_5O_6S$: 671; Found 672(M+H).

Similarly the following additional examples are prepared using commercially available sulfonyl chloride and Intermediate 9 according to the same procedure shown in the preparation of example 14.

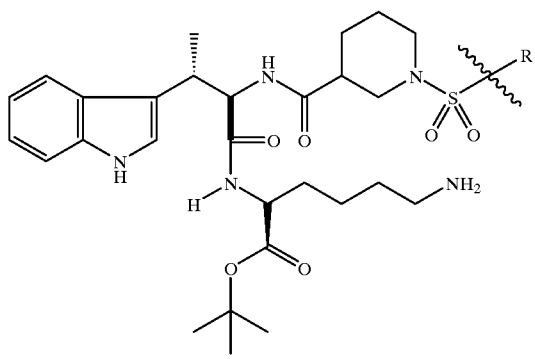

| Entry | R | ESI-MS (M + 1) |
|---|---|---|
| 1 | 3,4-dimethoxyphenyl | 714 |
| 2 | 2-thienyl | 660 |
| 3 | tert-butyl | 620 |

EXAMPLE 15

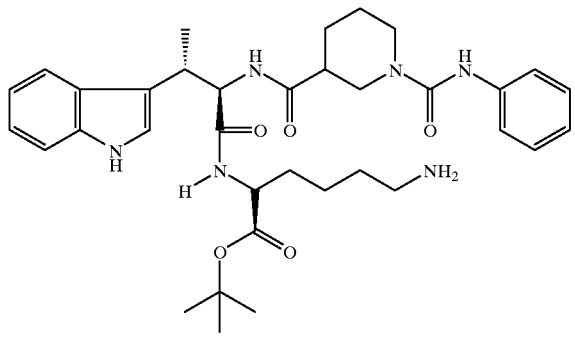

A mixture of Intermediate 9 resin (50 mg, 0.05 mmol), phenyl isocyanate (30 mg, 0.25 mmol) and DCM (2 mL) in a capped vial was shaken for 3 h. The resin was filtered, washed with DCM (3×5 mL), MeOH (2×5 mL), DCM (3×5 mL) and ether (2×5 mL). After dried over $N_2$ flow, the resin was heated at 40° C. with 2.0 mL of acetic acid in a capped vial overnight, filtered, washed with acetic acid (2×2 mL). The filtrates were combined and lyophilized to give the title compound as acetic acid salt (11 mg).

ESI-MS calc. for C35H48N6O5: 632; Found 633(M+H).

Similarly the following additional examples are prepared using commercially available isocyanate and Intermediate 9 according to the same procedure shown in the preparation of example 15.

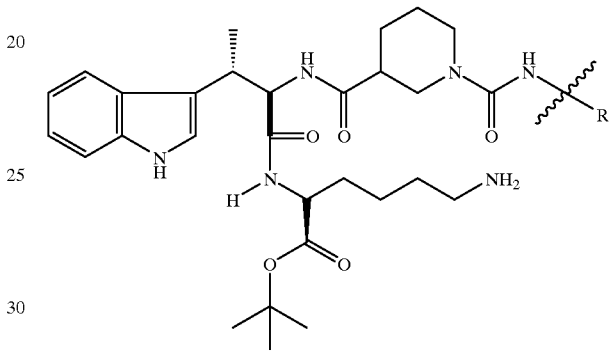

| Entry | R | ESI-MS (M + 1) |
|---|---|---|
| 1 | cyclohexyl | 639 |
| 2 | tert-butyl | 599 |
| 3 | benzyl methyl ester | 719 |
| 4 | 3-methoxyphenyl | 663 |

EXAMPLE 16

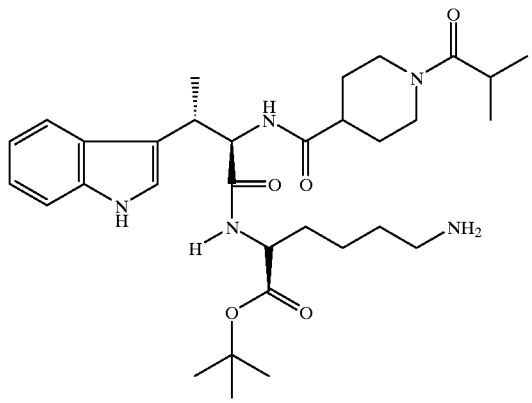

The title compound as a HCl salt (11.3 mg) was prepared by coupling Intermediate 10 (200 mg, 0.373 mmol) and Intermediate 18 (74.5 mg, 0.373 mmol) according to the general procedure 1 and then subjected to General procedure 2 to remove the Cbz protecting group.

ESI-MS calc. for C32H49N5O5: 583; Found 584(M+H).

EXAMPLE 17

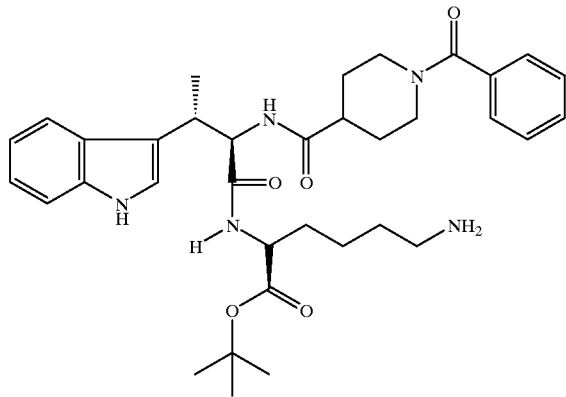

The title compound as a HCl salt (120 mg) was prepared by coupling Intermediate 10 (200 mg, 0.373 mmol) and Intermediate 17 (73 mg, 0.373 mmol) according to the general procedure 1 and then subjected to General procedure 2 to remove the Cbz protecting group.

ESI-MS calc. for C35H47N5O5: 617; Found 618(M+H).

EXAMPLE 18

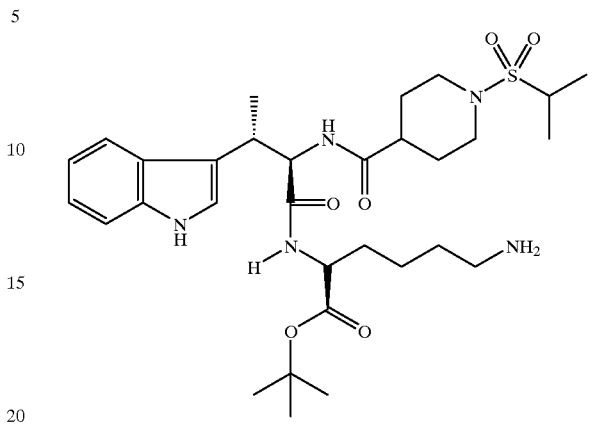

The title compound as a HCl salt (67 mg) was prepared by coupling intermediate 10 (200 mg, 0.373 mmol) and Intermediate 19 (101.4 mg, 0.373 mmol) according to the general procedure 1 and then subjected to General procedure 2 to remove the Cbz protecting group.

ESI-MS calc. for C31H49N5O6S: 619; Found 620(M+H).

EXAMPLE 19

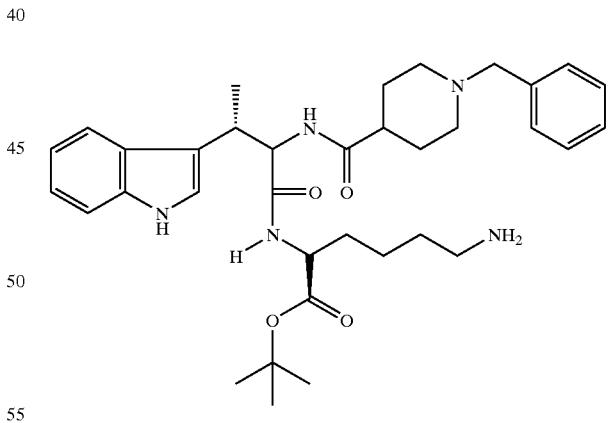

The title compound as a HCl salt (100 mg) was prepared by coupling Intermediate 10 (200 mg, 0.31 mmol) and Intermediate 16 (68 mg, 0.31 mmol) according to the general procedure 1 and then subjected to General procedure 2 to remove the Cbz protecting group.

ESI-MS calc. for C35H49N5O4: 603; Found 604(M+H).

EXAMPLE 20

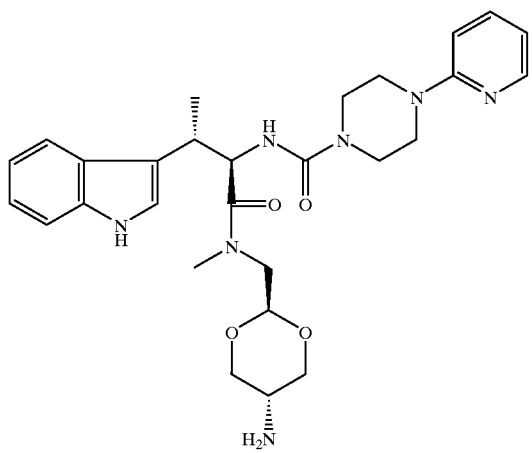

The title compound as a HCl salt (193 mg) was prepared by coupling Intermediate 4 (232 mg, 0.4 mmol) and N-2-pyridylpiperizane (65 mg, 0.4 mmol) according to the general procedure 3 and then subjected to General procedure 2 to remove the Cbz protecting group.

ESI-MS calc. for C28H37N7O4: 535; Found 536 (M+H).

Similarly the following additional examples are prepared using commercially available piperizane and Intermediate 4 according to the same procedure shown in the preparation of example 20.

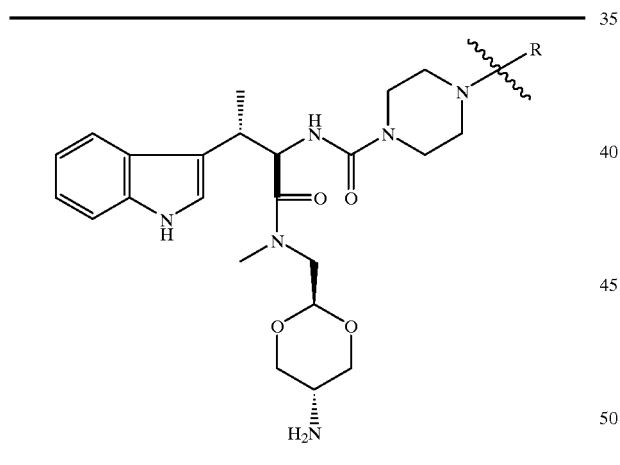

| Entry | R | ESI-MS (M + 1) |
|---|---|---|
| 1 | 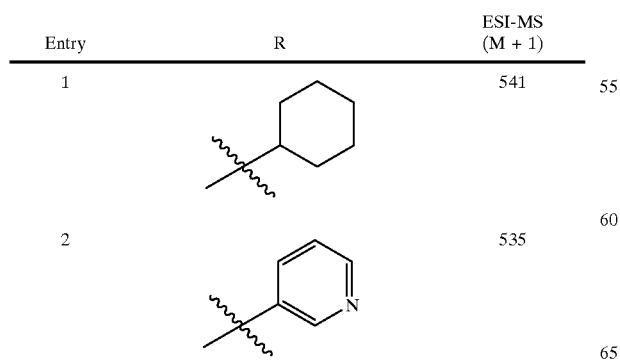 | 541 |
| 2 | | 535 |

-continued

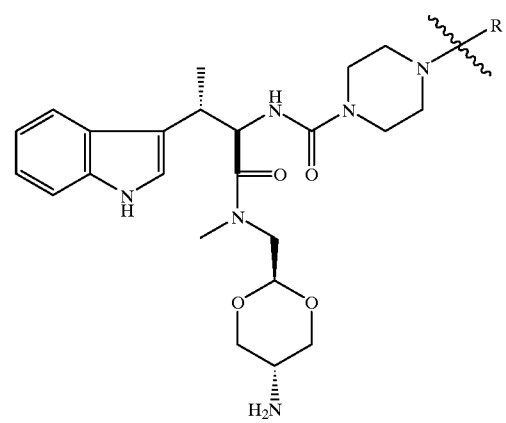

| Entry | R | ESI-MS (M + 1) |
|---|---|---|
| 3 | 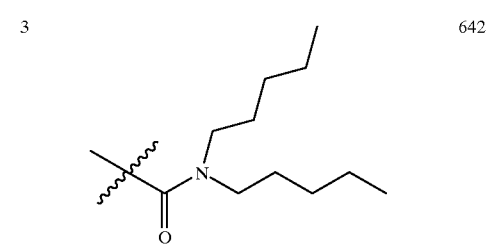 | 642 |
| 4 | 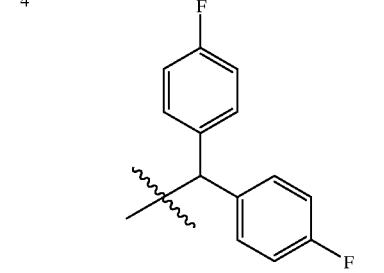 | 661 |
| 5 | | 553 |
| 6 | 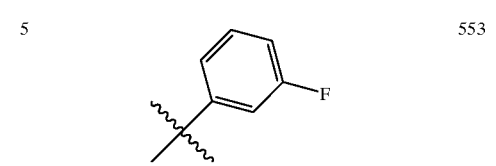 | 593 |
| 7 | 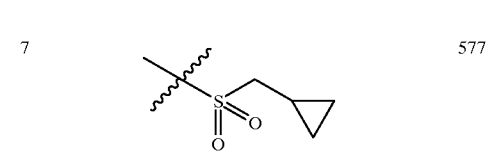 | 577 |

53

-continued

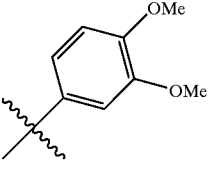

| Entry | R | ESI-MS (M + 1) |
|---|---|---|
| 8 | 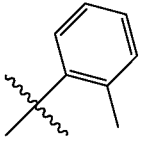 OMe, OMe | 595 |
| 9 | 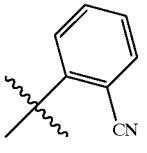 | 549 |
| 10 | 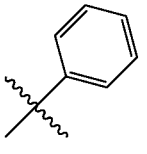 CN | 560 |
| 11 | 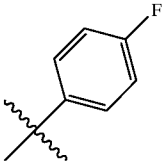 | 535 |
| 12 | 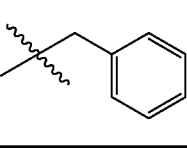 F | 553 |
| 13 | 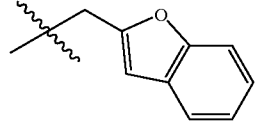 | 549 |

54

EXAMPLE 21

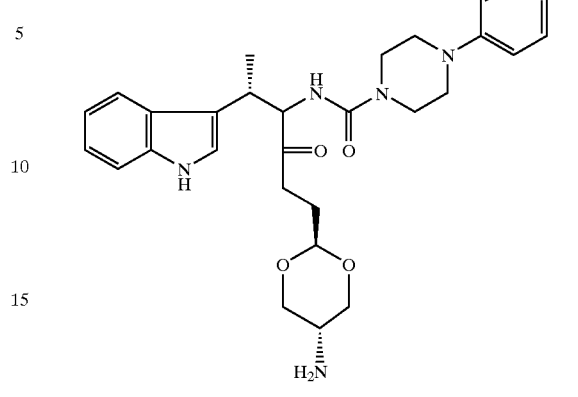

The title compound as a HCl salt (200 mg, 0.35 mmol) was prepared by coupling Intermediate 3 ( 2 mg, 0.4 mmol) and N-4-fluorophenylpiperizane (65 mg, 0.4 mmol) according to the general procedure 3 and then subjected to General procedure 2 to remove the Cbz protecting group.

ESI-MS calc. for C28H35FN6O4: 538; Found 539 (M+H).

Similarly the following additional examples are prepared using commercially available piperizane and Intermediate 3 according to the same procedure shown in the preparation of example 21.

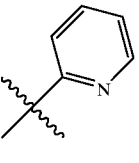

| Entry | R | ESI-MS (M + 1) |
|---|---|---|
| 1 | benzofuran-2-ylmethyl | 575 |
| 2 | pyridin-2-ylmethyl | 522 |

-continued

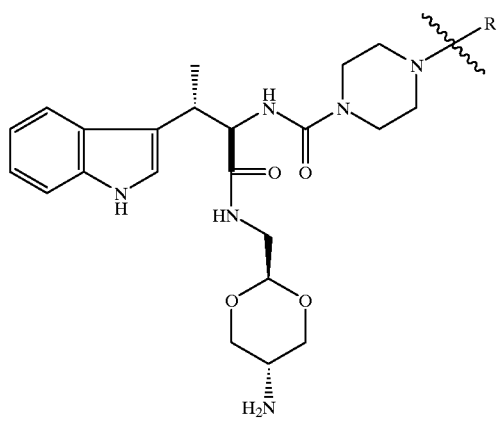

| Entry | R | ESI-MS (M + 1) |
|---|---|---|
| 3 | 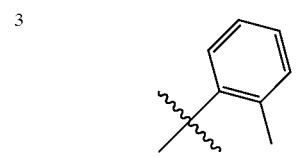 | 535 |
| 4 | 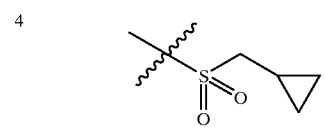 | 661 |
| 5 | 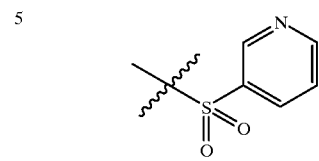 | 586 |
| 6 | 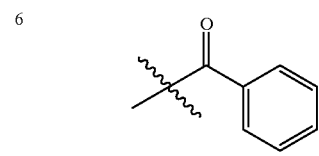 | 549 |
| 7 | 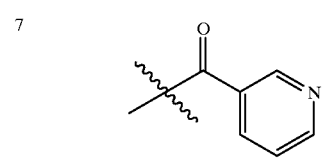 | 550 |
| 8 | 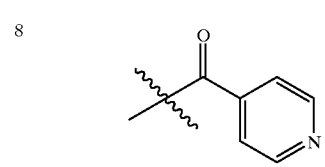 | 550 |

-continued

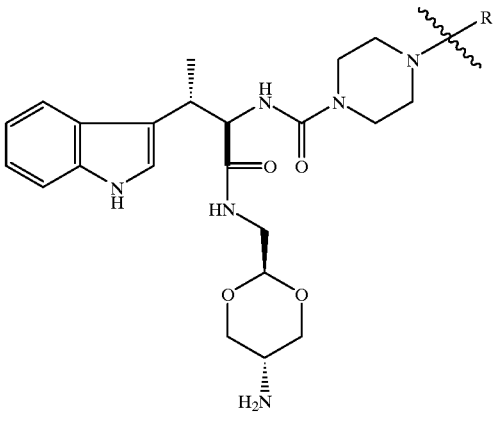

| Entry | R | ESI-MS (M + 1) |
|---|---|---|
| 9 | 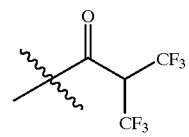 | 623 |

EXAMPLE 22

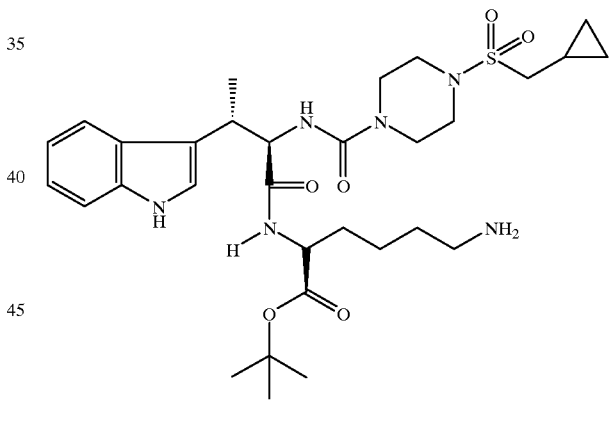

The title compound as a HCl salt (50 mg, 0.075 mmol) was prepared by coupling Intermediate 10 ( 95 mg, 0.15 mmol) and N-(cyclopropyl)-ethylsulfonyl-piperizane (65 mg, 0.4 mmol) according to the general procedure 3 and then subjected to General procedure 2 to remove the Cbz protecting group.

ESI-MS calc. for C31H48N6O6S: 632; Found 633 (M+H).

Similarly the following additional examples are prepared using commercially available piperizane and Intermediate 10 according to the same procedure shown in the preparation of example 22.

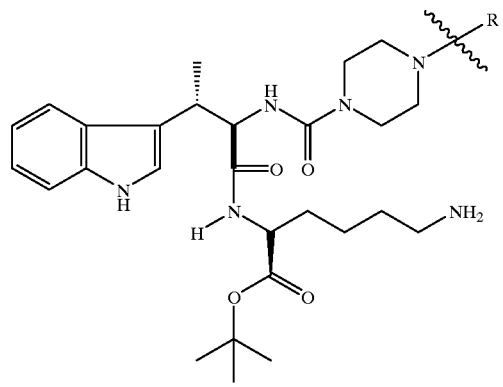
| Entry | R | ESI-MS (M + 1) | Entry | R | ESI-MS (M + 1) |
|---|---|---|---|---|---|
| 1 | -SO2-Et | 607 | 10 | -CO-CH(NH2)-CH2Ph | 662 |
| 3 | -SO2-iPr | 621 | 11 | -CO-iPr | 585 |
| 3 | -SO2-nBu | 635 | 12 | -CO-(2,2,3,3-tetramethylcyclopropyl) | 639 |
| 4 | -SO2-nPr | 621 | 13 | -CO-Ph | 619 |
| 5 | -SO2-Ph | 654 | 14 | -CO-C(CH3)2-NH2 | 600 |
| 6 | -CO-CH(CF3)-CF3 | 693 | 15 | -CO-CH2-CF3 | 545 |

-continued
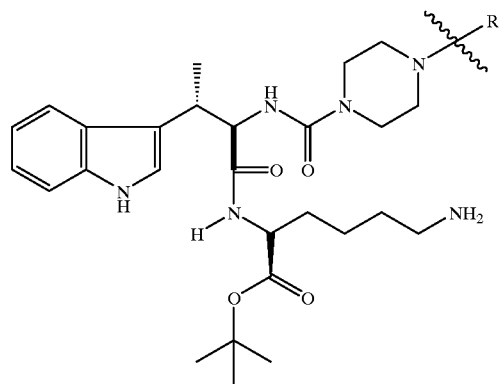
| Entry | R | ESI-MS (M + 1) | Entry | R | ESI-MS (M + 1) |
|---|---|---|---|---|---|
| 7 | -C(CH₃)(H)-C(=O)-O-CH(CF₃)₂ | 709 | 16 | -C(CH₃)(H)-C(=O)-NH-CH₂CF₃ | 640 |
| 8 | -C(CH₃)(H)-C(=O)-O-CH₂CF₃ | 641 | 17 | 2-(N,N-dimethylcarbamoyl)phenyl | 698 |
| 9 | -C(CH₃)(H)-C(=O)-CF₃ | 611 | 18 | cyclohexyl | 597 |
| 10 | (1H-indol-3-yl)methyl | 644 | 19 | cycloheptyl | 611 |
| 11 | benzyl | 605 | 20 | 2-methylphenyl | 605 |
| 12 | (1,3-benzodioxol-5-yl)methyl | 649 | 21 | diphenylmethyl | 681 |

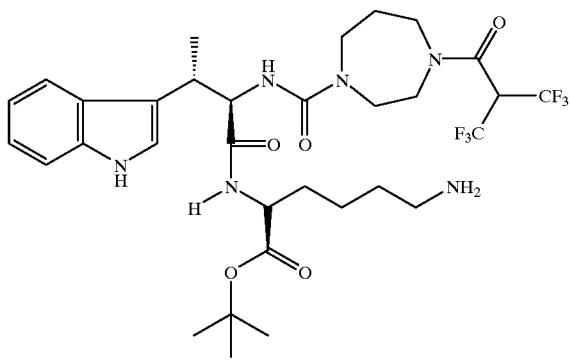

EXAMPLE 23

The title compound as a HCl salt was prepared by coupling Intermediate 10 and the corresponding amine according to the general procedure 3 and then subjected to General procedure 2 to remove the Cbz protecting group.

ESI-MS calc. for C32H44F6N6O5: 706; Found 707 (M+H).

Biological Assays

The ability of compounds of the present invention to act as somatostatin agonist can be determined by the following in vitro assays, which is disclosed in Rens-Domiano, et al., Pharmacological Properties of Two Cloned Somatostatin Receptors, *Mol. Pharm.*, 42:28–34 (1992) and incorporated herein.

Receptor Expression Constructs

Mammalian expression vectors containing full length coding sequences for hSSTR1–5 were constructed as follows: Fragments of genomic DNA carrying the various human somatostatin receptors were inserted into the multiple cloning site of pcDNA3 (Invitrogen). The fragments used were a 1.5-kb PstI-XmnI fragment for hSSTR1, 1.7-kb Bam-HI-HindIII fragment for hSSTR2, 2.0-kb NcoI-HindIII fragment for hSSTR3, a 1.4-kb NheI-NdeI fragment for hSSTR4, and a 3.2-kb XhoI-EcoRI fragment for hSSTR5.

Transfection

CHO-K1 cells were obtained from American Type Culture Collection (ATCC) and grown in alpha-MEM containing 10% fetal calf serum. Cells were stably transfected with DNA for all 5 hSSTRs using lipofectamine. Neomycin resistant clones were selected and maintained in medium containing G418 (400 μg ml).

Receptor Binding Assay

Cells were harvested 72 hr after transfection to 50 mM Tris-HCl, pH 7.8, containing 1 mM EGTA, 5 mM MgCl$_2$, 10 μg/ml leupeptin, 10 μg/ml pepstatin, 200 μg/ml bacitracin, and 0.5 μg/ml aprotinin (buffer 1) and were centrifuged at 24,000×g for 7 min at 4°. The pellet was homogenized in buffer 1 using a Brinkman Polytron (setting 2.5, 30 sec). The homogenate was then centrifuged at 48,000 μg for 20 min at 4° C. The pellet was homogenized in buffer 1 and the membranes were used in the radioligand binding assay. Cell membranes (approximately 10 μg of protein) were incubated with $^{125}$I-Tyr$^{11}$-somatostatin (0.2 nM; specific activity, 2000 Ci/mmol; NEN) in the presence or absence of competing peptides, in a final volume of 200 μl, for 30 min at 25°. Nonspecific binding was defined as the radioactivity remaining bound in the presence of 100 nM somatastatin. The binding reaction was terminated by the addition of ice-cold 50 nM Tris-HCl buffer, pH 7.8, and rapid filtration with 12 ml of ice-cold Tris HCl buffer, and the bound radioactivity was counted in a gamma scintillation spectrophotometer (80% efficiency). Data from radioligand binding studies were used to generate inhibition curves. IC$_{50}$ values were obtained from curve-fitting performed with the mathematical modeling program FITCOMP, available through the National Institutes of Health-sponsored PROPHET System.

Inhibition of Forskolin-stimulated cAMP Accumulation

Cells used for cAMP accumulation studies were subcultured in 12-well culture plates. COS-7 cells were transfected 72 hr before the experiments. Culture medium was removed from the wells and replaced with 500 μl of fresh medium containing 0.5 mM isobutylmethylxanthine. Cells were incubated for 20 min at 37°. Medium was then removed and replaced with fresh medium containing 0.5 mM isobutylmethylxanthine, with or without 10 μM forskolin and various concentrations of test compound. Cells were incubated for 30 min at 37°. Medium was then removed, and cells were sonicated in the wells in 500 μL of 1 N HCl and frozen for subsequent determination of cAMP content by radioimmunassay. Samples were thawed and diluted in cAMP radioimmunassay buffer before analysis of cAMP content using the commercially available assay kit from NEW/DuPont (Wilmington, Del.).

Inhibition of Growth Hormone Release

Functional activity of the various compounds was evaluated by quantitating release of growth hormone secretion from primary cultures of rat anterior pituitary cells. Cells were isolated from rat pituitaries by enzymatic digestion with 0.2% collagenase and 0.2% hyaluronidase in Hank's balanced salt solution. The cells were suspended in culture medium and adjusted to a concentration of 1.5×10$^5$ cells per milliliter, and 1.0 ml of this suspension was placed in each well of a 24-well tray. Cells were maintained in a humidified 5% CO$_2$-95% air atmosphere at 37° C. for 3 to 4 days. The culture medium consisted of Dulbecco's modified Eagle's medium containing 0.37% NaHCO$_3$, 10% horse serum, 2.5% fetal bovine serum, 1% nonessential amino acids, 1% glutamine, 1% nystatin, and 0.1% gentamycin. Before testing compounds for their capacity to inhibit GH release, cells were washed twice 1.5 hours before and once more immediately before the start of the experiment with the above culture medium containing 25 mM Hepes (pH 7.4). The compounds of the instant invention were tested in quadruplicate by adding them in 1 ml of fresh medium to each well and incubating them at 37° C. for 15 min. After incubation, the medium was removed and centrifuged at 2000 g for 15 min to remove any cellular material. The supernatant fluid was removed and assayed for GH by radioimmunoassay.

The compounds of this invention were found to inhibit the binding of somatostatin to its receptor at an IC$_{50}$ of about 30 pM to about 3 μM.

What is claimed is:

1. A compound represented by structural formula I:

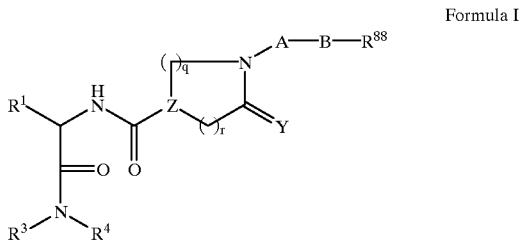

Formula I wherein:

R¹ is

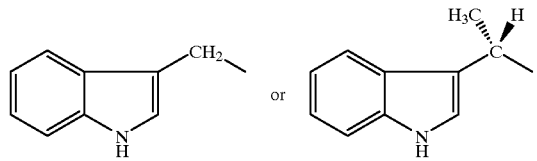

and is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$;

R² & R⁵ are selected from hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl; aryl is defined within;

Aryl is an aromatic ring selected from phenyl and naphthyl;

Heteroaryl is a monocyclic aromatic hydrocarbon group having 5 or 6 ring atoms, or a bicyclic aromatic group having 8 to 10 atoms, containing at least one heteroatom selected from O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms;

$R^{2a}$ is selected from the group consisting of hydrogen and $C_1$–$C_3$ alkyl, said alkyl optionally substituted by hydroxyl;

R³ is selected from the group consisting of H, $C_{1-8}$ alkyl, $(CH_2)_t$ aryl and $(CH_2)_t$ heteroaryl;

R⁴ is $CH(CO_2R^2)(CH_2)_nN(R^2)_2$, $CH(R^2)$—$(CH_2)_nN(R^2)_2$, $CH(CO_2R^2)$, $CHCON(R^2)_2$, $CH(CO_2R^2)CH_2W(CH_2)_nN(R^2)_2$, $CHR^2(CH_2)_nW(CH_2)_nN(R^2)_2$, or is selected from $R^6$;

R⁶ is:

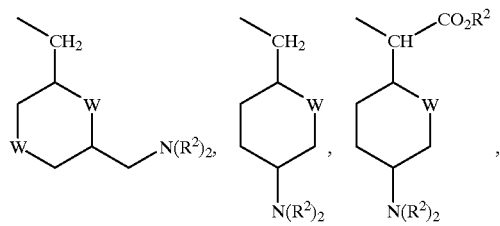

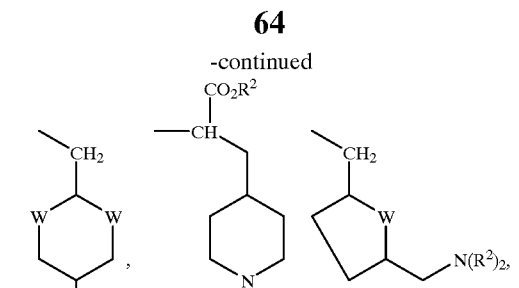

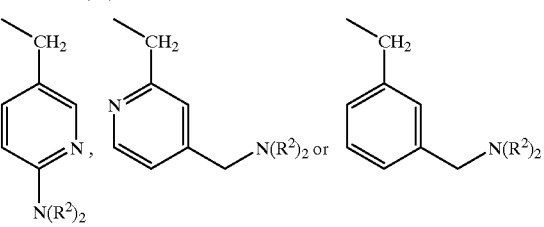

wherein R⁶ is optionally substituted with 1 to 3 groups of R², 1 to 3 of halogen, 1 to 2 of —$OR^2$, methylenedioxy, —$S(O)_mR^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)SO_2R^2$; or optionally,

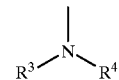

represents one of the following:

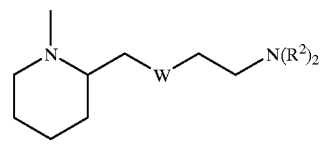

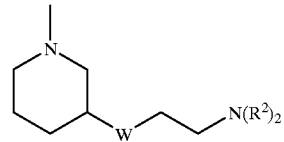

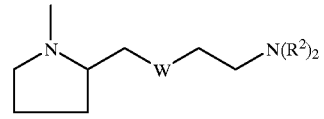

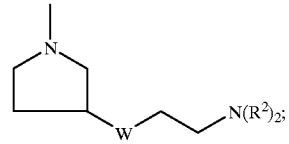

where W is selected from the group consisting of O, S, $CH_2$, $N(R^2)C(O)$ and $C(O)N(R^2)$;

Y is (H, H) or O;

Z is CH;

A is CO, $SO_2$,

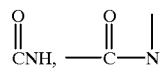

(alkyl having 1–6 carbons), $(CH_2)_x C_{3-8}$ cycloalkyl, $C_{3-8}$ cycloalkyl, aryl, heteroaryl, $(CH_2)_x$ aryl, $(CH_2)_x$ heteroaryl, heterocyclyl, $C_1$–$C_6$ alkyl, wherein x is 1–6, wherein each aryl, heteroaryl, heterocyclyl, and cycloalkyl is optionally substituted with 1–6 substituents independently selected from halogen, methylenedioxy, alkyl having 1–6 carbon atoms, O-alkyl having from 1–6 carbon atoms, OH, CN,

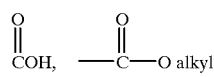

having 1–6 carbon atoms,

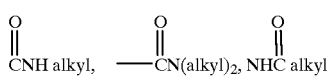

having 1–6 carbon atoms, wherein each alkyl that is either A or is a substituent on A is optionally substituted with 1–6 halogen atoms and optionally 1–3 substituents selected from aryl, OH, $NH_2$, cycloalkyl optionally having 1–4 $C_1$–$C_3$ alkyl groups,

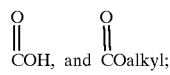

B is $C_1$–$C_6$ alkyl, $C_{3-8}$cycloalkyl, NH, N(alkyl having 1–6 carbon atoms), O, or a single bond, wherein $C_{3-8}$cycloalkyl is optionally substituted with 1–6 substituents independently selected from halogen, methylenedioxy, alkyl having 1–6 carbon atoms, O-alkyl having 1–6 carbon atoms,

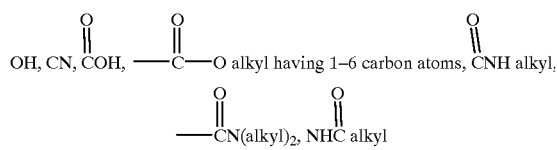

having 1–6 carbon atoms, wherein each alkyl that is either B or is a substituent on B is optionally substituted with 1–6 halogen atoms and optionally 1–3 substituents selected from aryl, OH, $NH_2$, $C_3$–$C_8$cycloalkyl optionally having 1–4 $C_1$–$C_3$ alkyl groups,

and $R^{88}$ is H, aryl, $(CH_2)_x$ aryl, heteroaryl, $(CH_2)_x$ heteroaryl, $C_3$–$C_8$ cycloalkyl, $(CH_2)_x$ cycloalkyl having 3–8 carbons, $C_1$–$C_6$ alkyl, NH alkyl having 1–6 carbon atoms, $N(alkyl)_2$, where each alkyl is independently a $C_1$–$C_6$ alkyl,

having 1–6 carbons, where x is 1–6 and each aryl, heteroaryl, and cycloalkyl is optionally substituted with 1–6 substituents independently selected from halogen, methylenedioxy, alkyl having 1–6 carbon atoms, O-alkyl having from 1–6 carbon atoms, OH, CN,

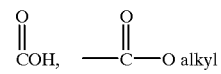

having 1–6 carbon atoms,

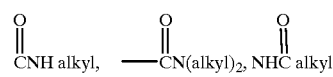

having 1–6 carbon atoms, wherein each alkyl that is either $R^{88}$ or is a substituent on $R^{88}$ is optionally substituted with 1–6 halogen atoms and optionally 1–3 substituents selected from aryl, OH, $NH_2$, cycloalkyl optionally having 1–4 $C_1$–$C_3$ alkyl groups;

m is an integer from 0 to 2;

n is an integer from 0–5;

q is 3;

r is 0; and t is an integer from 0 to 3.

2. A compound according to claim 1 having a structural formula Ia:

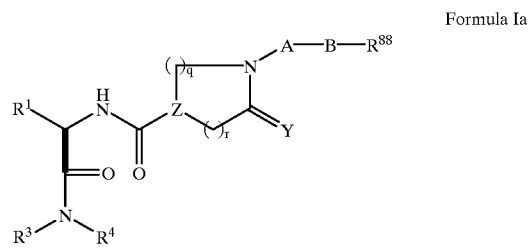

Formula Ia wherein:

$R^2$ is selected from: hydrogen, $C_1$–$C_8$ alkyl, and $(CH_2)_t$ aryl, where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^3$ is selected from the group consisting of hydrogen, $C_1$–$C_8$ alkyl and $(CH_2)_t$ aryl;

$R^4$ is $CH(CO_2R^2)(CH_2)_n N(R^2)_2$, $CH(R^2)$—$(CH_2)_n N(R^2)_2$, $CH(CO_2R^2)CH_2WCH_2CH_2N(R^2)_2$, or is selected from $R^6$;

$R^6$ is

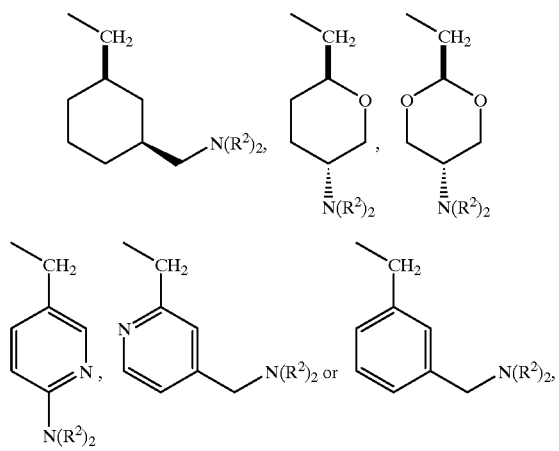

wherein $R^6$ is optionally substituted with 1 to 3 groups of $R^2$, 1 to 3 of halogen, 1 to 2 of —$OR^2$, 1 to 2 of —$CF_3$, —$OCF_3$, nitro, —$C(O)OR^2$, or —$C(O)N(R^2)(R^2)$; or optionally,

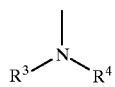

can be

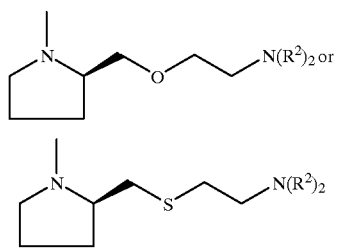

and all other variables are described above.

3. A compound according to claim 2 wherein:

$R^1$ is

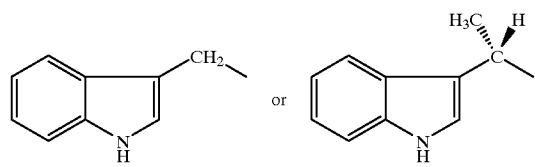

which may be substituted by 1 to 3 of $R^2$, 1 to 3 of halogen, 1 to 2 of —$OR^2$, 1 to 2 of —$CF_3$, —$OCF_3$, nitro, —$C(O)OR^2$, —$C(O)N(R^2)(R^2)$;

$R^3$ is selected from hydrogen or methyl;

$R^4$ is $CH(CO_2But)(CH_2)_4NH_2$, $CH(R^2)$—$(CH_2)_4NH_2$, $CH(CO_2But)CH_2WCH_2CH_2NH_2$, or is $R^6$ wherein $R^6$ is

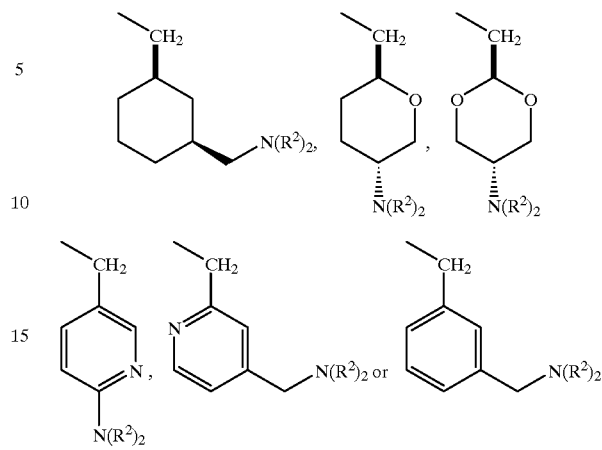

which is optionally substituted with 1 to 3 groups of $R^2$, 1 to 3 of halogen, 1 to 2 of —$OR^2$, 1 to 2 of —$CF_3$;

and all other variables are described above.

4. A compound according to claim 3; wherein Y is (H, H).

5. A method of treating or controlling diabetes in a mammal in need of such treatment, which comprises administering to said mammal an effective amount of a somatostatin agonist of claim 1.

6. A method of treating acromegaly in a mammal in need of such treatment, which comprises administering to said mammal an effective amount of a somatostatin agonist of claim 1.

7. A method of treating restenosis in a mammal in need of such treatment, which comprises administering to said mammal an effective amount of a somatostatin agonist of claim 1.

8. A method of treating retinopathy in a mammal in need of such treatment, which comprises administering to said mammal an effective amount of a somatostatin agonist of claim 1.

9. A method of treating depression in a mammal in need of such treatment, which comprises administering to said mammal an effective amount of a somatostatin agonist of claim 1.

10. A pharmaceutical composition comprising a compound according to claim 1 and a pharmaceutically acceptable carrier.

11. A compound according to claim 1 selected from the group consisting of:

| Entry | R | ESI-MS (M+1) |
|---|---|---|
| 1 | 3-F-benzyl | 622 |
| 2 | 3,4-diF-benzyl | 640 |
| 3 | 3-(CO2Me)-benzyl | 662 |
| 4 | 2-phenylbenzyl | 680 |
| 5 | 3-OMe-benzyl | 634 |
| 6 | 4-Cl-benzodioxol-5-ylmethyl | 682 |
| 7 | diphenylmethyl | 680 |
| 8 | naphth-2-ylmethyl | 654 |
| 9 | 2,3-diF-benzyl | 640 |

| Entry | R | ESI-MS (M + 1) |
|---|---|---|
| 1 | 3,4-methylenedioxyphenyl | 662 |
| 2 | pyridin-3-yl | 619 |
| 3 | 1H-benzimidazol-5-yl | 658 |
| 4 | 3-acetamidophenyl | 675 |
| 5 | (3,4-methylenedioxyphenyl)methyl | 676 |
| 6 | 3,5-difluorobenzyl | 668 |
| 7 | diphenylmethyl | 708 |
| 8 | hydroxydiphenylmethyl | 724 |
| 9 | 2,4-dimethylpentan-2-yl | 598 |

| Entry | R | ESI-MS (M + 1) |
|---|---|---|

-continued

| | 1 | | OMe, OMe substituted phenyl | 714 |
|---|---|---|---|---|
| | 2 | | 2-thienyl | 660 |
| | 3 | | isobutyl | 620 | and

| Entry | R | ESI-MS (M + 1) |
|---|---|---|
| 1 | cyclohexyl | 639 |
| 2 | isopropyl | 599 |

-continued

| | 3 | | benzyl with methyl ester | 719 |
|---|---|---|---|---|
| | 4 | | 3-methoxyphenyl | 663 |

12. A compound according to claim 1 as shown below:

* * * * *